(12) United States Patent
Zhu et al.

(10) Patent No.: US 7,879,997 B2
(45) Date of Patent: Feb. 1, 2011

(54) COMPOUNDS FOR THE TREATMENT OF INFLAMMATORY DISORDERS

(75) Inventors: Zhaoning Zhu, Plainsboro, NJ (US); Robert D. Mazzola, Jr., Stewartsville, NJ (US); Wensheng Yu, Edison, NJ (US); Joseph A. Kozlowski, Princeton, NJ (US)

(73) Assignee: Schering Corporation, Kenilworth, NJ (US)

( * ) Notice: Subject to any disclaimer, the term of this patent is extended or adjusted under 35 U.S.C. 154(b) by 638 days.

(21) Appl. No.: 11/502,116

(22) Filed: Aug. 10, 2006

(65) Prior Publication Data

US 2007/0191332 A1   Aug. 16, 2007

Related U.S. Application Data

(60) Provisional application No. 60/707,653, filed on Aug. 12, 2005.

(51) Int. Cl.
*C07D 205/08* (2006.01)
*A61K 31/397* (2006.01)

(52) U.S. Cl. ............................ 540/200; 514/210.02

(58) Field of Classification Search .................. 540/200; 514/210.02
See application file for complete search history.

(56) References Cited

U.S. PATENT DOCUMENTS

| | | | |
|---|---|---|---|
| 5,420,298 | A | 5/1995 | Edwards et al. |
| 6,114,361 | A | 9/2000 | Robinson et al. |
| 6,838,466 | B2 | 1/2005 | Zhu et al. |
| 7,279,485 | B2 * | 10/2007 | Cheng et al. ............. 514/275 |
| 7,482,370 | B2 | 1/2009 | Yu et al. |
| 7,488,745 | B2 | 2/2009 | Yu et al. |
| 7,504,424 | B2 | 3/2009 | Yu et al. |
| 7,524,842 | B2 | 4/2009 | Lavey et al. |
| 2002/0137734 | A1 | 9/2002 | Chen et al. |
| 2005/0113344 | A1 | 5/2005 | Li et al. |
| 2006/0178366 | A1 | 8/2006 | Siddiqui et al. |
| 2006/0252778 | A1 | 11/2006 | Guo et al. |
| 2007/0265299 | A1 | 11/2007 | Lavey et al. |
| 2008/0226618 | A1 | 9/2008 | Mansoor et al. |
| 2009/0111803 | A1 | 4/2009 | Yu et al. |
| 2009/0137586 | A1 | 5/2009 | Yu et al. |
| 2009/0156586 | A1 | 6/2009 | Lavey et al. |
| 2009/0170875 | A1 | 7/2009 | Yu et al. |

FOREIGN PATENT DOCUMENTS

| | | |
|---|---|---|
| EP | 0574758 | 12/1993 |
| EP | 1099690 | 5/2001 |
| EP | 1 138 680 | 10/2001 |
| GB | 2268934 | 1/1994 |
| WO | WO94/24140 | 10/1994 |
| WO | WO95/09841 | 4/1995 |
| WO | WO 00/05204 | * 2/2000 |
| WO | WO03/053940 | 7/2003 |
| WO | WO 2005/077937 | 8/2005 |

OTHER PUBLICATIONS

Uenaka et al. (WO 00/05204 CAPLUS Abstract Accession No. 2000:84762).*
Adlington et al. (Journal of Medicinal Chemistry (2001), 44(10), 1491-1508).*
PCT International Search Report mailed date Jan. 17, 2007 for corresponding PCT Application No. PCT/US2006/031151.
Joseph A. Kozlowski et al., U.S. Appl. No. 12/388,984, filed Feb. 19, 2009 (Claims).

* cited by examiner

*Primary Examiner*—Robert Havlin
(74) *Attorney, Agent, or Firm*—Eric A. Meade; Krishna G. Banerjee

(57) ABSTRACT

This invention relates to compounds of the Formula (I):

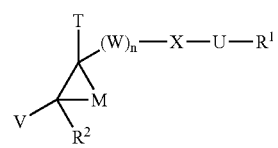

or a pharmaceutically acceptable salt, solvate or isomer thereof, wherein n, M, V, T, W, X, U, $R^1$ and $R^2$ are as disclosed in the present specification, and which compounds are useful for the treatment of diseases or conditions mediated by MMPs, TNF-α or combinations thereof.

9 Claims, No Drawings

COMPOUNDS FOR THE TREATMENT OF INFLAMMATORY DISORDERS

This Application claims the benefit of U.S. Provisional Application Ser. No. 60/707,653, filed Aug. 12, 2005, which is incorporated herein by reference in its entirety.

BACKGROUND OF THE INVENTION

1. Field of the Invention

This invention relates to hydroxamic or carboxylic acid functional compounds that can inhibit the production of tumor necrosis factor alpha (TNF-α), pharmaceutical compositions comprising such compounds, and methods of treatment using such compounds.

2. Description

Tumor necrosis factor alpha (TNF-α) has been shown to play a pivotal role in immune and inflammatory responses. Inappropriate or over-expression of TNF-α is a hallmark of a number of diseases, including rheumatoid arthritis (RA), Crohn's disease and sepsis. Inhibition of TNF-α production has been shown to be beneficial in many preclinical models of inflammatory disease, making inhibition of TNF-α production or signaling an appealing target for the development of novel anti-inflammatory drugs.

Tumor necrosis factor alpha is a cell-associated cytokine that is processed from a 26 kd precursor form to a 17 kd active form. See Black R. A. "Tumor necrosis factor-alpha converting enzyme" Int J Biochem Cell Biol. January 2002; 34(1): 1-5 and Moss M L, White J M, Lambert M H, Andrews R C. "TACE and other ADAM proteases as targets for drug discovery" Drug Discov Today. Apr. 1, 2001; 6(8):417-426, each of which is incorporated by reference herein.

TNF-α has been shown to be a primary mediator in humans and animals of inflammation, fever and acute phase responses, similar to those observed during acute infection and shock. Excess TNF-α has been shown to be lethal. Blocking the effects of TNF-α with specific antibodies can be beneficial in a variety of conditions, including autoimmune diseases such as rheumatoid arthritis (Feldman et al, Lancet, (1994) 344, 1105), non-insulin dependent diabetes mellitus (Lohmander L. S. et al., Arthritis Rheum. 36 (1993) 1214-22) and Crohn's disease (Macdonald T. et al., Clin. Exp. Immunol. 81 (1990) 301).

Metalloproteinases (MP) are important in the uncontrolled breakdown of connective tissue, including proteoglycan and collagen, leading to resorption of the extracellular matrix. This is a feature of many pathological conditions, such as rheumatoid and osteo-arthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMP (tissue inhibitor of metalloproteinase), which form inactive complexes with the MP's.

Osteo- and rheumatoid arthritis (OA and RA, respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A (1970) 424-434). There are four classes of protein degradative enzymes in mammalian cells: serine, cysteine, aspartic and metalloproteinases. The available evidence supports that it is the metalloproteinases that are responsible for the degradation of the extracellular matrix of articular cartilage in OA and RA. Increased activities of collagenases and stromelysin have been found in OA cartilage and the activity correlates with severity of the lesion (Mankin et al. Arthritis Rheum. 21, 1978, 761-766, Woessner et al. Arthritis Rheum. 26, 1983, 63-68 and Ibid. 27, 1984, 305-312). In addition, aggrecanase (a newly identified metalloproteinase enzymatic activity) has been identified that provides the specific cleavage product of proteoglycan, found in RA and OA patients (Lohmander L. S. et al. Arthritis Rheum. 36, 1993, 1214-22).

Therefore, metalloproteinases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. Ann. Rep. Med. Chem. 25, 175-184, AP, San Diego, 1990).

Compounds that inhibit the production of TNF-α are therefore of therapeutic importance for the treatment of inflammatory disorders. Recently it has been shown that a matrix metalloproteinase (MMP) or family of metalloproteinases, hereafter known as TNF-α convertases (TACE), as well as other MP's are capable of converting TNF-α from its inactive to active form (Gearing et al Nature, 1994, 370, 555). Since excessive TNF-α production has been noted in several disease conditions also characterized by MMP-mediated tissue degradation, compounds which inhibit both MMPs and TNF-α production may also have a particular advantage in diseases where both mechanisms are involved.

U.S. Pat. No. 6,838,466 refers to hydroxamic or carboxylic acid functional compounds that can inhibit the production of tumor necrosis factor alpha (TNF-α).

WO03/053940 refers to barbituric acid derivatives useful as TNF-α converting enzyme (TACE) and matrix metalloproteinase (MMP) inhibitors.

WO95/09841 describes compounds that are hydroxamic acid derivatives and are inhibitors of cytokine production.

European Patent Application Publication No. 574,758 A1, discloses hydroxamic acid derivatives as collagenase inhibitors. GB 2 268 934 A and WO 94/24140 claim hydroxamate inhibitors of MMPs as inhibitors of TNF-α production.

There is a need in the art for inhibitors of MMPs, in particular TNF-α convertase, which can be useful as anti-inflammatory compounds and cartilage protecting therapeutics. The inhibition of TNF-α convertase and other metalloproteinases can prevent the degradation of cartilage by these enzymes, thereby alleviating the pathological conditions of osteo- and rheumatoid arthritis.

SUMMARY OF THE INVENTION

In its many embodiments, the present invention provides a novel class of compounds as inhibitors of TACE, the production of TNF-α, MMPs, ADAMs or any combination thereof, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with TACE, TNF-α, MMPs, ADAMs or any combination thereof using such compounds or pharmaceutical compositions.

In one embodiment, the present application discloses a compound having the general structure shown in Formula (I):

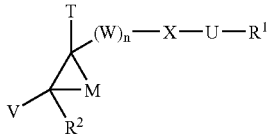

(I)

or a pharmaceutically acceptable salt, solvate or ester thereof, wherein:

M, together with the two carbon atoms to which it is shown attached in formula (I) is 4-7 membered heterocyclyl or heterocyclenyl comprising 0-3 carbonyl groups, 0-3 double bonds, and 1-3 heteroatoms selected from O, N, and S, wherein said 4-7 membered heterocyclyl or heterocyclenyl can, in addition to the four substituents V, $R^2$, T, and —(W)$_n$—X—U—$R^1$ as set forth in formula (I), be further optionally substituted with $R^{21}$;

T is selected from the group consisting of H, alkyl, $R^{21}$-substituted alkyl, cycloalkyl, aryl, heteroaryl, heterocyclyl, arylalkyl, heteroarylalkyl, —$OR^3$, —$C(O)R^4$, —$C(O)OR^3$, —$C(O)NR^{24}R^{25}$, —$C(O)NR^{24}OR^3$, —$C(O)SR^3$, —$NR^{24}R^{25}$, —$NR^{25}C(O)R^4$, —$NR^{25}C(O)OR^3$, —$NR^{25}C(O)NR^{24}R^{25}$, —$NR^{25}C(O)NR^{24}OR^3$, —$SR^3$, —$N(R^{24})S(O)_2R^{25}$, —$S(O)_xNR^{24}R^{25}$, —$S(O)_xNR^{25}OR^3$, —CN, —$P(O)(R^{24})(OR^{24})$, —$P(O)(OR^{24})(OR^{24})$, —$C(R^4)(=N(OR^3))$, —$C(O)$—$N(R^{31})CH(R^{32})$—$C(O)NR^{24}R^{25}$ and —$C(O)N(R^{31})CH(R^{32})$—$C(O)$—$NR^{25}OR^3$, wherein each of the cycloalkyl, aryl, heteroaryl, heterocyclyl, arylalkyl and heteroarylalkyl groups of T is unsubstituted or optionally independently substituted with one to six $R^{20}$ moieties which can be the same or different, each $R^{20}$ moiety being independently selected from the group of $R^{20}$ moieties below;

V is selected from the group consisting of alkyl, $R^{21}$-substituted alkyl, cycloalkyl, heterocyclyl, arylalkyl, heteroarylalkyl, aryl, heteroaryl, —$OR^3$, —$C(O)R^4$, —$(CR^{23}R^{24})_{n1}C(O)OR^3$, —$C(O)NR^{24}R^{25}$, —$(CR^{23}R^{24})_{n1}C(O)NR^{25}OR^3$, —$C(O)SR^3$, —$C(R^{23})(R^{24})SH$, —$NR^{24}R^{25}$, —$NR^{25}C(O)R^4$, —$NR^{25}C(O)OR^3$, —$NR^{25}C(O)NR^{24}R^{25}$, —$NR^{25}C(O)NR^{24}OR^3$, —$SR^3$, —$S(O)_xNR^{24}R^{25}$, —$S(O)_xNR^{25}OR^3$, —CN, —$P(O)(R^{25})(OR^{24})$, —$P(O)(OR^{24})(OR^{24})$, —$C(R^4)(=N(OR^3))$, —$C(O)$—$N(R^{31})CH(R^{32})$—$C(O)N^{24}R^{25}$ and —$C(O)N(R^{31})CH(R^{32})$—$C(O)$—$NR^{25}OR^3$, wherein each of the cycloalkyl, heterocyclyl, arylalkyl, heteroarylalkyl, aryl and heteroaryl groups of V is unsubstituted or optionally independently substituted with one to three $R^{20}$ moieties which can be the same or different, each $R^{20}$ moiety being independently selected from the group of $R^{20}$ moieties below;

W is selected from the group consisting of

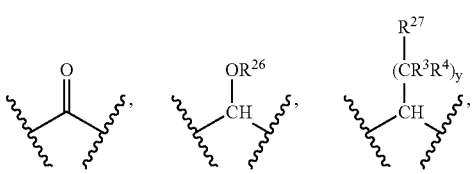

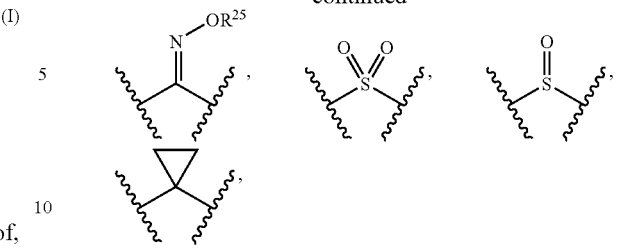

a covalent bond, —$(C(R^3)(R^4))_{n2}$—, —O—, —S—, —$N(R^{24})$—, and —$N(Z)$—;

X is selected from the group consisting of alkyl, cycloalkyl, heterocyclyl, arylalkyl, heteroarylalkyl, aryl, heteroaryl and —C≡C—, wherein each of the alkyl, cycloalkyl, heterocyclyl, arylalkyl, heteroarylalkyl, aryl, and heteroaryl groups of X is unsubstituted or optionally independently substituted with one to four selected $R^{20}$ moieties which can be the same or different, each $R^{20}$ moiety being independently selected from the group of $R^{20}$ moieties below, U is selected from the group consisting of a covalent bond, —$(C(R^3)(R^4))_p$—, —Y—$(C(R^3)(R^4))_q$—, —$(C(R^3)(R^4))_t$—Y—, —$N(R^3)(Z)$-Q-, -Q-$N(R^3)(Z)$— and —Y—;

Q is selected from the group consisting of —S(O)—, —$S(O)_2$—, —C(O)—, and —$C(O)NR^4$—;

Y is selected from the group consisting of —O—, —$S(O)_x$—, —N(Z)—, —$N(R^4)(Z)$; —C(O)—, —OC(O)—, —$C(O)N(R^{24})$—, —$N(R^{24})C(O)N(R^{25})$—, —$N(R^{24})S(O)$—, —$N(R^{24})S(O)_2$—, —$S(O)N(R^{24})$—, and —$S(O)_2N(R^{24})$—;

Z is selected from the group consisting of —$R^3$, —$C(O)R^3$, —$S(O)_xR^3$ and —$C(O)NR^3R^4$;

n is 0 to 2;
n1 is 0 to 2;
n2 is 1 to 2;
p is 1 to 4;
q is 1 to 4;
t is 1 to 4;
v is 1 to 3;
x is 0 to 2;
y is 0 to 3;

$R^1$ is selected from the group consisting of alkyl, $R^{21}$-substituted alkyl, cycloalkyl, heterocyclyl, arylalkyl, heteroarylalkyl, aryl, heteroaryl, —C≡$CR^3$ and —$CR^3$=$CR^4R^5$, wherein each of the alkyl, cycloalkyl, heterocyclyl, arylalkyl, heteroarylalkyl, aryl and heteroaryl groups of $R^1$ is unsubstituted or optionally independently substituted with one to six $R^{20}$ moieties which can be the same or different, each $R^{20}$ moiety being independently selected from the group of $R^{20}$ moieties below, each of $R^2$, $R^4$ and $R^5$ is the same or different and each is independently selected from the group consisting of H, halo, alkyl, $R^{22}$-substituted alkyl, cycloalkyl, heterocyclyl, arylalkyl, heteroarylalkyl, aryl, heteroaryl, —$OR^6$, —$C(O)R^7$, —$C(O)OR^6$, —$NR^{24}R^{25}$, —$NR^{24}C(O)R^{25}$, —N(=C—O—$NR^{24}R^{25}$) and —$NR^{24}S(O)_2R^{25}$, wherein each of the cycloalkyl, heterocyclyl, arylalkyl, heteroarylalkyl, aryl and heteroaryl groups of $R^2$, $R^4$ and $R^5$ is unsubstituted or optionally independently substituted with one to six alkyl, $R^{22}$-substituted alkyl or $R^{22}$ moieties which can be the same or different, each $R^{22}$ moiety being independently selected from the group of $R^{22}$ moieties below;

each $R^3$ is the same or different and is independently selected from the group consisting of H, alkyl, $R^{22}$-substituted alkyl, heterocyclyl, arylalkyl, heteroarylalkyl, aryl, heteroaryl, —$OR^6$, —$C(O)R^7$, —$C(O)OR^6$, —$NR^{24}R^{25}$, —$NR^{24}C(O)R^{25}$, —$N(=C-O-NR^{24}R^{25})$ and —$NR^{24}S(O)_2R^{25}$, wherein each of the cycloalkyl, heterocyclyl, arylalkyl, heteroarylalkyl, aryl and heteroaryl groups of $R^3$ is unsubstituted or optionally independently substituted with one to four alkyl, $R^{22}$-substituted alkyl or $R^{22}$ moieties which can be the same or different, each $R^{22}$ moiety being independently selected from the group of $R^{22}$ moieties below;

each $R^6$ is independently selected from the group consisting of H, alkyl and —$OCF_3$;

each $R^7$ is independently selected from the group consisting of H, alkyl, heteroaryl and —$CF_3$;

each $R^{20}$ is independently selected from the group consisting of: alkyl, $R^{21}$-substituted alkyl, —$OR^3$, halo, (=O), —CN, —$NO_2$, —$NR^{24}R^{25}$, —$C(O)R^3$, —$C(O)OR^3$, —$C(O)NR^{24}R^{25}$, —$S(O)_xNR^{24}R^{25}$, —$S(O)_xR^5$, —$CF_3$, —$OCF_3$, —$CF_2CF_3$, —CH(=NOH), —C(=NOH)$R^3$, aryl, heteroaryl, cycloalkyl, heterocyclyl, —$N(R^{25})S(O)_xR^5$, —$N(R^{25})C(O)R^5$, and —$N(R^{25})C(O)NR^{24}R^{25}$, wherein each of the aryl, heteroaryl, cycloalkyl and heterocyclyl groups of $R^{20}$ is unsubstituted or optionally independently substituted with one to four $R^{22}$ moieties which can be the same or different, each $R^{22}$ moiety being independently selected from the group of $R^{22}$ moieties below, or two $R^{20}$ groups taken together with the carbon to which both $R^{20}$ groups are attached is

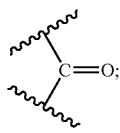

$R^{21}$ is one to three substituents independently selected from the group consisting of: —$OR^3$, halo, —CN, —$NO_2$, —$NR^{24}R^{25}$, —$C(O)R^3$, —$C(O)OR^3$, —$C(O)NR^{24}R^{25}$, —$S(O)_xNR^{24}R^{25}$, —$SO_xR^5$, —$CF_3$, —$OCF_3$, —$CF_2CF_3$, —C(=NOH)$R^3$, $R^{23}$-substituted alkyl, aryl, heteroaryl, cycloalkyl, heterocyclyl, —$N(R^{25})S(O)_xR^5$, —$N(R^{25})C(O)R^5$, and —$N(R^{25})C(O)NR^{24}R^{25}$;

wherein each of the aryl, heteroaryl, cycloalkyl, and heterocyclyl groups of $R^{21}$ is unsubstituted or optionally independently substituted with one to four $R^{23}$ moieties which can be the same or different, each $R^{23}$ moiety being independently selected from the group of $R^{23}$ moieties below, or two $R^{21}$ groups taken together with the carbon to which both $R^{21}$ groups are attached is

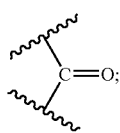

each $R^{22}$ is independently selected from the group consisting of: halo, alkynyl, aryl, heteroaryl, —$OR^{24}$, —($C_1$-$C_6$ alkyl)-$OR^{24}$, —CN, —$NO_2$, —$NR^{24}R^{25}$, —$C(O)R^{23}$, —$C(O)OR^{23}$, —$C(O)NR^{24}R^{25}$, —$S(O)_xNR^{24}R^{25}$, —$S(O)_x$ $R^{23}$, —$CF_3$, —$OCF_3$, —$CF_2CF_3$, —C(=NOH)$R^{23}$, —$N(R^{24})S(O)_xR^{25}$, —$N(R^{24})C(O)R^{25}$, and —$N(R^{24})C(O)NR^{24}R^{25}$, or two $R^{22}$ groups taken together with the carbon to which both $R^{22}$ groups are attached is

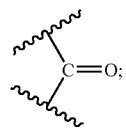

each $R^{23}$ is independently selected from the group consisting of H, hydroxyl, halo and alkyl;

each $R^{24}$ is independently selected from the group consisting of H and alkyl;

each $R^{25}$ is independently selected from the group consisting of H, hydroxyl, alkyl, hydroxyalkyl, aryl, cycloalkyl, heteroaryl, —$NR^{24}R^{24}$, —($C_1$ to $C_6$ alkyl)$NR^{24}N^{24}$, —$CF_3$ and —$S(O)_xR^{23}$;

$R^{26}$ is selected from the group consisting of H, alkyl, cycloalkyl, aryl, and heteroaryl;

$R^{27}$ is selected from the group consisting of H, alkyl, cycloalkyl, aryl, and heteroaryl; and each of $R^{31}$ and $R^{32}$ is the same or different and wherein each is independently selected from the group consisting of H, alkyl, cycloalkyl, aryl, heteroaryl, —$NR^{24}R^{25}$, —$(CH_2)_3NH(C=NH)NH_2$, —$CH_2C(O)NH_2$, —$CH_2C(O)OH$, —$CH_2SH$, —$CH_2S-SCH_2CH(NH_2)C(O)OH$, —$CH_2CH_2C(O)OH$, —$CH_2CH_2C(O)NH_2$, —$(CH_2)_4NH_2$, —$CH_2CH_2CH(OH)CH_2NH_2$, —$CH_2CH(CH_3)_2$, —CH($CH_3$)$CH_2$($CH_3$), —$CH_2CH_2SCH_3$, —$CH_2OH$, —CH(OH)($CH_3$),

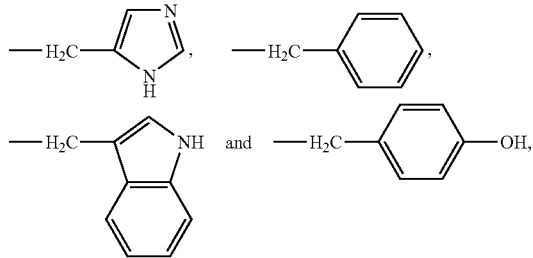

or $R^{31}$ and $R^{32}$, together with the N to which $R^{31}$ is attached and the C to which $R^{31}$ is attached, form a 5-membered ring which is unsubstituted or optionally independently substituted with a hydroxyl group.

In another embodiment, the present invention discloses a compound represented by the structural formula (II):

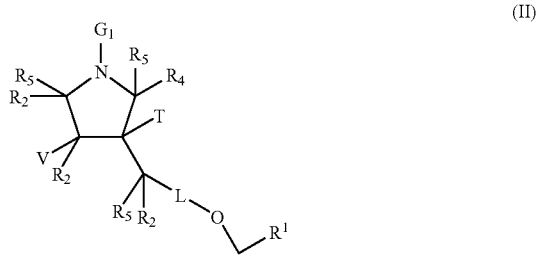

or a pharmaceutically acceptable salt, solvate or ester of said compound, wherein:

L is aryl or heteroaryl;

$R^1$ is selected from the group consisting of alkyl, $R^{21}$-substituted alkyl, cycloalkyl, heterocyclyl, arylalkyl, heteroarylalkyl, aryl, heteroaryl, —C≡$CR^3$ and —$CR^3$=$CR^4R^5$, wherein each of the alkyl, cycloalkyl, heterocyclyl, arylalkyl, heteroarylalkyl, aryl and heteroaryl groups of $R^1$ is unsubstituted or optionally independently substituted with one to six $R^{20}$ moieties which can be the same or different, each $R^{20}$ moiety being independently selected from the group of $R^{20}$ moieties below, T is selected from the group consisting of H, alkyl, $R^{21}$-substituted alkyl, cycloalkyl, aryl, heteroaryl, heterocyclyl, arylalkyl, heteroarylalkyl, —$OR^3$, —C(O)$R^4$, —C(O)$OR^3$, —C(O)$NR^{24}R^{25}$, —C(O)$NR^{24}OR^3$, —C(O)$SR^3$, —$NR^{24}R^{25}$, —$NR^{25}$C(O)$R^4$, —$NR^{25}$C(O)$OR^3$, —$NR^{25}$C(O)$NR^{24}R^{25}$, —$NR^{25}$C(O)$NR^{24}OR^3$, —$SR^3$, —N($R^{24}$)S(O)$_2R^{25}$, —S(O)$_x$$NR^{24}R^{25}$, —S(O)$_x$$NR^{25}OR^3$, —CN, —P(O)($R^{24}$)($OR^{24}$), —P(O)($OR^{24}$)($OR^{24}$), —C($R^4$)(=N($OR^3$)), —C(O)—N($R^{31}$)CH($R^{32}$)—C(O)$NR^{24}R^{25}$ and —C(O)N($R^{31}$)CH($R^{32}$)—C(O)—$NR^{25}OR^3$, wherein each of the cycloalkyl, aryl, heteroaryl, heterocyclyl, arylalkyl and heteroarylalkyl groups of T is unsubstituted or optionally independently substituted with one to six $R^{20}$ moieties which can be the same or different, each $R^{20}$ moiety being independently selected from the group of $R^{20}$ moieties below;

$G_1$ is O, H, alkyl, $R^{21}$-substituted alkyl, —$OR^3$, halo, —C(O)$R^3$, —C(O)$OR^3$, —C(O)$NR^{24}R^{25}$, —S(O)$_x$$NR^{24}R^{25}$, —S(O)$_x$$R^5$, —$CF_3$, —$OCF_3$, —$CF_2CF_3$, —C(=NOH)$R^3$, aryl, heteroaryl, cycloalkyl, heterocyclyl, and heteroarylalkyl, wherein each of the aryl, heteroaryl, cycloalkyl, heterocyclyl and heteroarylalkyl groups of P is unsubstituted or optionally independently substituted with one to four $R^{23}$ moieties which can be the same or different, each $R^{23}$ moiety being independently selected from the group of $R^{23}$ moieties below, V is selected from the group consisting of alkyl, $R^{21}$-substituted alkyl, cycloalkyl, heterocyclyl, arylalkyl, heteroarylalkyl, aryl, heteroaryl, —$OR^3$, —C(O)$R^4$, —($CR^{23}R^{24}$)$_{n1}$C(O)$OR^3$, —C(O)$NR^{24}R^{25}$, —($CR^{23}R^{24}$)$_{n1}$C(O)$NR^{25}OR^3$, —C(O)$SR^3$, —C($R^{23}$)($R^{24}$)SH, —$NR^{24}R^{25}$, —$NR^{25}$C(O)$R^4$, —$NR^{25}$C(O)$OR^3$, —$NR^{25}$C(O)$NR^{24}R^{25}$, —$NR^{25}$C(O)$NR^{24}OR^3$, —$SR^3$, —S(O)$_x$$NR^{24}R^{25}$, —S(O)$_x$$NR^{25}OR^3$, —CN, —P(O)($R^{25}$)($OR^{24}$), —P(O)($OR^{24}$)($OR^{24}$), —C($R^4$)(=N($OR^3$)), —C(O)—N($R^{31}$)CH($R^{32}$)—C(O)$NR^{24}R^{25}$ and —C(O)N($R^{31}$)CH($R^{32}$)—C(O)—$NR^{25}OR^3$, wherein each of the cycloalkyl, heterocyclyl, arylalkyl, heteroarylalkyl, aryl and heteroaryl groups of V is unsubstituted or optionally independently substituted with one to three $R^{20}$ moieties which can be the same or different, each $R^{20}$ moiety being independently selected from the group of $R^{20}$ moieties below;

n1 is 0 to 2;

x is 0 to 2;

each of $R^2$, $R^4$ and $R^5$ is the same or different and each is independently selected from the group consisting of H, halo, alkyl, $R^{22}$-substituted alkyl, cycloalkyl, heterocyclyl, arylalkyl, heteroarylalkyl, aryl, heteroaryl, —$OR^6$, —C(O)$R^7$, —C(O)$OR^6$, —$NR^{24}R^{25}$, —$NR^{24}$C(O)$R^{25}$, —N(=C—O—$NR^{24}R^{25}$), —$NR^{24}$S(O)$_2R^{25}$, wherein each of the cycloalkyl, heterocyclyl, arylalkyl, heteroarylalkyl, aryl and heteroaryl groups of $R^2$, $R^4$ and $R^5$ is unsubstituted or optionally independently substituted with one to six alkyl, $R^{22}$-substituted alkyl or $R^{22}$ moieties which can be the same or different, each $R^{22}$ moiety being independently selected from the group of $R^{22}$ moieties below, or $R^4$ and $R^5$ taken together with the carbon to which both $R^4$ and $R^5$ are attached is

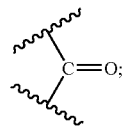

each $R^3$ is the same or different and is independently selected from the group consisting of H, alkyl, $R^{22}$-substituted alkyl, heterocyclyl, arylalkyl, heteroarylalkyl, aryl, heteroaryl, —$OR^6$, —C(O)$R^7$, —C(O)$OR^6$, —$NR^{24}R^{25}$, —$NR^{24}$C(O)$R^{25}$, —N(=C—O—$NR^{24}R^{25}$) and —$NR^{24}$S(O)$_2R^{25}$, wherein each of the cycloalkyl, heterocyclyl, arylalkyl, heteroarylalkyl, aryl and heteroaryl groups of $R^3$ is unsubstituted or optionally independently substituted with one to four alkyl, $R^{22}$-substituted alkyl or $R^{22}$ moieties which can be the same or different, each $R^{22}$ moiety being independently selected from the group of $R^{22}$ moieties below;

each $R^6$ is independently selected from the group consisting of H, alkyl and —$OCF_3$;

each $R^7$ is independently selected from the group consisting of H, alkyl, heteroaryl and —$CF_3$;

each $R^{20}$ is independently selected from the group consisting of: alkyl, $R^{21}$-substituted alkyl, —$OR^3$, halo, —CN, —$NO_2$, —$NR^{24}R^{25}$, —C(O)$R^3$, —C(O)$OR^3$, —C(O)$NR^{24}R^{25}$, —S(O)$_x$$NR^{24}R^{25}$, —S(O)$_x$$R^5$, —$CF_3$, —$OCF_3$, —$CF_2CF_3$, —C(=NOH)$R^3$, aryl, heteroaryl, cycloalkyl, heterocyclyl, —N($R^{25}$)S(O)$_x$$R^5$, —N($R^{25}$)C(O)$R^5$, and —N($R^{25}$)C(O)$NR^{24}R^{25}$, wherein each of the aryl, heteroaryl, cycloalkyl and heterocyclyl groups of $R^{20}$ is unsubstituted or optionally independently substituted with one to four $R^{22}$ moieties which can be the same or different, each $R^{22}$ moiety being independently selected from the group of $R^{23}$ moieties below, or two $R^{20}$ groups taken together with the carbon to which both $R^{20}$ groups are attached is

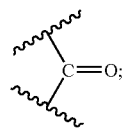

$R^{21}$ is one to three substituents independently selected from the group consisting of: —$OR^3$, halo, —CN, —$NO_2$, —$NR^{24}R^{25}$, —C(O)$R^3$, —C(O)$OR^3$, —C(O)$NR^{24}R^{25}$, —S(O)$_x$$NR^{24}R^{25}$, —$SO_xR^5$, —$CF_3$, —$OCF_3$, —$CF_2CF_3$, —C(=NOH)$R^3$, $R^{23}$-substituted alkyl, aryl, heteroaryl, cycloalkyl, heterocyclyl, —N($R^{25}$)S(O)$_x$$R^5$, —N($R^{25}$)C(O)$R^5$, and —N($R^{25}$)C(O)$NR^{24}R^{25}$;

wherein each of the aryl, heteroaryl, cycloalkyl, and heterocyclyl groups of $R^{21}$ is unsubstituted or optionally independently substituted with one to four $R^{23}$ moieties which can be the same or different, each $R^{23}$ moiety being independently selected from the group of $R^{23}$ moieties below, or two $R^{21}$ groups taken together with the carbon to which both $R^{21}$ groups are attached is

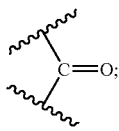

each $R^{22}$ is independently selected from the group consisting of: halo, alkynyl, aryl, heteroaryl, —$OR^{24}$, —($C_1$-$C_6$ alkyl)—$OR^{24}$, —CN, —$NO_2$, —$NR^{24}R^{25}$, —$(O)R^{23}$, —$C(O)OR^{23}$, —$C(O)NR^{24}R^{25}$, —$S(O)_xNR^{24}R^{25}$, —$S(O)_x R^{23}$, —$CF_3$, —$OCF_3$, —$CF_2CF_3$, —$C(=NOH)R^{23}$, —$N(R^{24})S(O)_xR^{25}$, —$N(R^{24})C(O)R^{25}$, and —$N(R^{24})C(O)NR^{24}R^{25}$, or two $R^{22}$ groups taken together with the carbon to which both $R^{22}$ groups are attached is

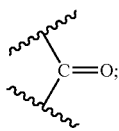

each $R^{23}$ is independently selected from the group consisting of H, hydroxyl, halo and alkyl;

each $R^{24}$ is independently selected from the group consisting of H and alkyl;

each $R^{25}$ is independently selected from the group consisting of H, hydroxyl, alkyl, hydroxyalkyl, aryl, cycloalkyl, heteroaryl, —$NR^{24}R^{24}$, —($C_1$ to $C_6$ alkyl)$NR^{24}N^{24}$, —$CF_3$ and —$S(O)_xR^{23}$;

each of $R^{31}$ and $R^{32}$ is the same or different and wherein each is independently selected from the group consisting of H, alkyl, cycloalkyl, aryl, heteroaryl, —$NR^{24}R^{25}$, —$(CH_2)_3NH(C=NH)NH_2$, —$CH_2C(O)NH_2$, —$CH_2C(O)OH$, —$CH_2SH$, —$CH_2S$—$SCH_2CH(NH_2)C(O)OH$, —$CH_2CH_2C(O)OH$, —$CH_2CH_2C(O)NH_2$, —$(CH_2)_4NH_2$, —$CH_2CH_2CH(OH)CH_2NH_2$, —$CH_2CH(CH_3)_2$, —$CH(CH_3)CH_2(CH_3)$, —$CH_2CH_2SCH_3$, —$CH_2OH$, —$CH(OH)(CH_3)$,

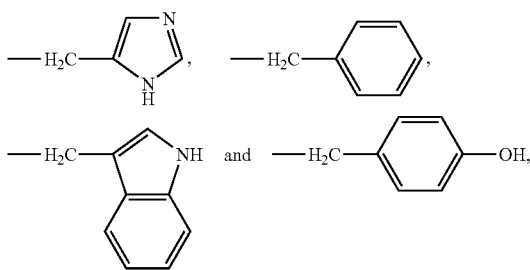

or $R^{31}$ and $R^{32}$, together with the N to which $R^{31}$ is attached and the C to which $R^{31}$ is attached, form a 5-membered ring which is unsubstituted or optionally independently substituted with a hydroxyl group.

In another embodiment, the present invention provides a compound of formula (III)

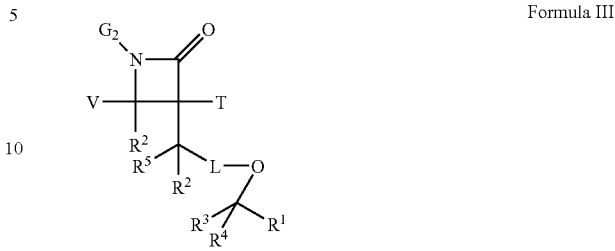

Formula III or a pharmaceutically acceptable salt, solvate or ester of said compound, wherein:

L is aryl or heteroaryl;

$R^1$ is selected from the group consisting of alkyl, $R^{21}$-substituted alkyl, cycloalkyl, heterocyclyl, arylalkyl, heteroarylalkyl, aryl, heteroaryl, —C≡$CR^3$ and —$CR^3$=$CR^4R^5$, wherein each of the alkyl, cycloalkyl, heterocyclyl, arylalkyl, heteroarylalkyl, aryl and heteroaryl groups of $R^1$ is unsubstituted or optionally independently substituted with one to six $R^{20}$ moieties which can be the same or different, each $R^{20}$ moiety being independently selected from the group of $R^{20}$ moieties below, T is selected from the group consisting of H, alkyl, $R^{21}$-substituted alkyl, cycloalkyl, aryl, heteroaryl, heterocyclyl, arylalkyl, heteroarylalkyl, —$OR^3$, $C(O)R^4$, —$C(O)OR^3$, —$C(O)NR^{24}R^{25}$, —$C(O)NR^{24}OR^3$, —$C(O)SR^3$, —$NR^{24}R^{25}$, —$NR^{25}C(O)R^4$, —$NR^{25}C(O)OR^3$, —$NR^{25}C(O)NR^{24}R^{25}$, —$NR^{25}C(O)NR^{24}OR^3$, —$SR^3$, —$N(R^{24})S(O)_2R^{25}$, —$S(O)_xNR^{24}R^{25}$, —$S(O)_xNR^{25}OR^3$, —CN, —$P(O)(R^{24})(OR^{24})$, —$P(O)(OR^{24})(OR^{24})$, —$C(R^4)(=N(OR^3))$, —$C(O)$—$N(R^{31})CH(R^{32})$—$C(O)NR^{24}R^{25}$ and —$C(O)N(R^{31})CH(R^{32})$—$C(O)$—$NR^{25}OR^3$, wherein each of the cycloalkyl, aryl, heteroaryl, heterocyclyl, arylalkyl and heteroarylalkyl groups of T is unsubstituted or optionally independently substituted with one to six $R^{20}$ moieties which can be the same or different, each $R^{20}$ moiety being independently selected from the group of $R^{20}$ moieties below;

$G_2$ is H, alkyl, $R^{21}$-substituted alkyl, —$OR^3$, halo, —$C(O)R^3$, —$C(O)OR^3$, —$C(O)NR^{24}R^{25}$, —$S(O)_xNR^{24}R^{25}$, —$S(O)_xR^5$, —$CF_3$, —$OCF_3$, —$CF_2CF_3$, —$C(=NOH)R^3$, aryl, heteroaryl, cycloalkyl, heterocyclyl, and heteroarylalkyl, wherein each of the aryl, heteroaryl, cycloalkyl, heterocyclyl and heteroarylalkyl groups of Q is unsubstituted or optionally independently substituted with one to four $R^{23}$ moieties which can be the same or different, each $R^{23}$ moiety being independently selected from the group of $R^{23}$ moieties below, V is selected from the group consisting of alkyl, $R^{21}$-substituted alkyl, cycloalkyl, heterocyclyl, arylalkyl, heteroarylalkyl, aryl, heteroaryl, —$OR^3$, —$C(O)R^4$, —$(CR^{23}R^{24})_{n1}C(O)OR^3$, —$C(O)NR^{24}R^{25}$, —$(CR^{23}R^{24})_{n1}C(O)NR^{25}OR^3$, —$C(O)SR^3$, —$C(R^{23})(R^{24})SH$, —$NR^{24}R^{24}$, —$NR^{25}C(O)R^4$, —$NR^{25}C(O)OR^3$, —$NR^{25}C(O)NR^{24}R^{25}$, —$NR^{25}C(O)NR^{24}OR^3$, —$SR^3$, —$S(O)_xNR^{24}R^{25}$, —$S(O)_xNR^{25}OR^3$, —CN, —$P(O)(R^{25})(OR^{24})$, —$P(O)(OR^{24})(OR^{24})$, —$C(R^4)(=N(OR^3))$, —$C(O)$—$N(R^{31})CH(R^{32})$—$C(O)NR^{24}R^{25}$ and —$C(O)N(R^{31})CH(R^{32})$—$C(O)$—$NR^{25}OR^3$, wherein each of the cycloalkyl, heterocyclyl, arylalkyl, heteroarylalkyl, aryl and heteroaryl groups of V is unsubstituted or optionally independently substituted with one to three $R^{20}$ moieties which can be the same or different, each $R^{20}$ moiety being independently selected from the group of $R^{20}$ moieties below;

n1 is 0 to 2;

x is 0 to 2;

each of $R^2$, $R^4$ and $R^5$ is the same or different and each is independently selected from the group consisting of H, halo, alkyl, $R^{22}$-substituted alkyl, cycloalkyl, heterocyclyl, arylalkyl, heteroarylalkyl, aryl, heteroaryl, —$OR^6$, —$C(O)R^7$, —$C(O)OR^6$, —$NR^{24}R^{25}$, —$NR^{24}C(O)R^{25}$, —$N(=C—O—NR^{24}R^{25})$, —$NR^{24}S(O)_2R^{25}$, wherein each of the cycloalkyl, heterocyclyl, arylalkyl, heteroarylalkyl, aryl and heteroaryl groups of $R^2$, $R^4$ and $R^5$ is unsubstituted or optionally independently substituted with one to six alkyl, $R^{22}$-substituted alkyl or $R^{22}$ moieties which can be the same or different, each $R^{22}$ moiety being independently selected from the group of $R^{22}$ moieties below, or $R^4$ and $R^5$ taken together with the carbon to which both $R^4$ and $R^5$ are attached is

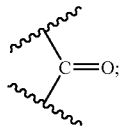

each $R^3$ is the same or different and is independently selected from the group consisting of H, alkyl, $R^{22}$-substituted alkyl, heterocyclyl, arylalkyl, heteroarylalkyl, aryl, heteroaryl, —$OR^6$, —$C(O)R^7$, —$C(O)OR^6$, —$NR^{24}R^{25}$, —$NR^{24}C(O)R^{25}$, —$N(=C—O—NR^{24}R^{25})$ and —$NR^{24}S(O)_2R^{25}$, wherein each of the cycloalkyl, heterocyclyl, arylalkyl, heteroarylalkyl, aryl and heteroaryl groups of $R^3$ is unsubstituted or optionally independently substituted with one to four alkyl, $R^{22}$-substituted alkyl or $R^{22}$ moieties which can be the same or different, each $R^{22}$ moiety being independently selected from the group of $R^{22}$ moieties below;

each $R^6$ is independently selected from the group consisting of H, alkyl and —$OCF_3$;

each $R^7$ is independently selected from the group consisting of H, alkyl, heteroaryl and —$CF_3$;

each $R^{20}$ is independently selected from the group consisting of: alkyl, $R^{21}$-substituted alkyl, —$OR^3$, halo, —CN, —$NO_2$, —$NR^{24}R^{25}$, —$C(O)R^3$, —$C(O)OR^3$, —$C(O)NR^{24}R^{25}$, —$S(O)_xNR^{24}R^{25}$, —$S(O)_xR^5$, —$CF_3$, —$OCF_3$, —$CF_2CF_3$, —$C(=NOH)R^3$, aryl, heteroaryl, cycloalkyl, heterocyclyl, —$N(R^{25})S(O)_xR^5$, —$N(R^{25})C(O)R^5$, and —$N(R^{25})C(O)NR^{24}R^{25}$, wherein each of the aryl, heteroaryl, cycloalkyl and heterocyclyl groups of $R^{20}$ is unsubstituted or optionally independently substituted with one to four $R^{22}$ moieties which can be the same or different, each $R^{22}$ moiety being independently selected from the group of $R^{23}$ moieties below, or two $R^{20}$ groups taken together with the carbon to which both $R^{20}$ groups are attached is

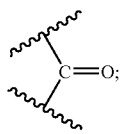

$R^{21}$ is one to three substituents independently selected from the group consisting of: —$OR^3$, halo, —CN, —$NO_2$, —$NR^{24}R^{25}$, —$C(O)R^3$, —$C(O)OR^3$, —$C(O)NR^{24}R^{25}$, —$S(O)_xNR^{24}R^{25}$, —$SO_xR^5$, —$CF_3$, —$OCF_3$, —$CF_2CF_3$, —$C(=NOH)R^3$, $R^{23}$-substituted alkyl, aryl, heteroaryl, cycloalkyl, heterocyclyl, —$N(R^{25})S(O)_xR^5$, —$N(R^{25})C(O)R^5$, and —$N(R^{25})C(O)NR^{24}R^{25}$;

wherein each of the aryl, heteroaryl, cycloalkyl, and heterocyclyl groups of $R^{21}$ is unsubstituted or optionally independently substituted with one to four $R^{23}$ moieties which can be the same or different, each $R^{23}$ moiety being independently selected from the group of $R^{23}$ moieties below, or two $R^{21}$ groups taken together with the carbon to which both $R^{21}$ groups are attached is

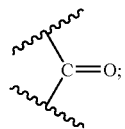

each $R^{22}$ is independently selected from the group consisting of: halo, alkynyl, aryl, heteroaryl, —$OR^{24}$, —$(C_1-C_6$ alkyl)-$OR^{24}$, —CN, —$NO_2$, —$NR^{24}R^{25}$, —$C(O)R^{23}$, —$C(O)OR^{23}$, —$C(O)NR^{24}R^{25}$, —$S(O)_xNR^{24}R^{25}$, —$S(O)_xR^{23}$, —$CF_3$, —$OCF_3$, —$CF_2CF_3$, —$C(=NOH)R^{23}$, —$N(R^{24})S(O)_xR^{25}$, —$N(R^{24})C(O)R^{25}$, and —$N(R^{24})C(O)NR^{24}R^{25}$, or two $R^{22}$ groups taken together with the carbon to which both $R^{22}$ groups are attached is

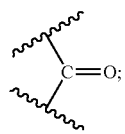

each $R^{23}$ is independently selected from the group consisting of H, hydroxyl, halo and alkyl;

each $R^{24}$ is independently selected from the group consisting of H and alkyl;

each $R^{25}$ is independently selected from the group consisting of H, hydroxyl, alkyl, hydroxyalkyl, aryl, cycloalkyl, heteroaryl, —$NR^{24}R^{24}$, —$(C_1$ to $C_6$ alkyl)$NR^{24}N^{24}$, —$CF_3$ and —$S(O)R^{23}$;

each of $R^{31}$ and $R^{32}$ is the same or different and wherein each is independently selected from the group consisting of H, alkyl, cycloalkyl, aryl, heteroaryl, —$NR^{24}R^{25}$, —$(CH_2)_3NH(C=NH)NH_2$, —$CH_2C(O)NH_2$, —$CH_2C(O)OH$, —$CH_2SH$, —$CH_2S—SCH_2CH(NH_2)C(O)OH$, —$CH_2CH_2C(O)OH$, —$CH_2CH_2C(O)NH_2$, —$(CH_2)_4NH_2$, —$CH_2CH_2CH(OH)CH_2NH_2$, —$CH_2CH(CH_3)_2$, —$CH(CH_3)CH_2(CH_3)$, —$CH_2CH_2SCH_3$, —$CH_2OH$, —$CH(OH)(CH_3)$,

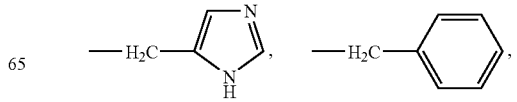

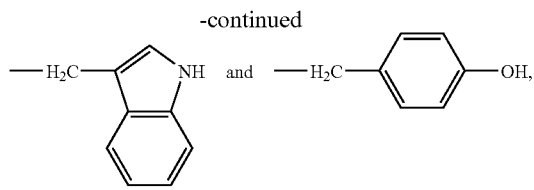

or $R^{31}$ and $R^{32}$, together with the N to which $R^{31}$ is attached and the C to which $R^{31}$ is attached, form a 5-membered ring which is unsubstituted or optionally independently substituted with a hydroxyl group.

The compounds of Formula I, II or III can be useful as inhibitors of and can be useful in the treatment and prevention of diseases associated with TACE, TNF-α, MMPs, ADAMs or any combination thereof.

DETAILED DESCRIPTION OF THE INVENTION

In its several embodiments, the present invention provides a novel class of inhibitors of MMP and TNF-α convertase, pharmaceutical compositions containing one or more of the compounds, methods of preparing pharmaceutical formulations comprising one or more such compounds, and methods of treatment, prevention or amelioration of one or more of the symptoms of inflammation.

In one embodiment, the present invention provides compounds which are represented by structural Formula (I), (II) or (III) above or a pharmaceutically acceptable salt, solvate or ester of any of Formula (I), (II) or (III), wherein the various moieties are as described above.

In one embodiment, in the compound of formula (I), n is 1.

In one embodiment, in the compound of formula (I), M, together with the two carbon atoms to which it is shown attached in formula (I), represents a 4-5 membered heterocyclyl or heterocyclenyl comprising 0-1 carbonyl groups, 0-1 double bonds, and 1 heteroatom selected from O, N, and S, wherein said 4-5 membered heterocyclyl can, in addition to the four substituents V, $R^2$, T, and —$(W)_n$—X—U—$R^1$ as set forth in formula (I), be further optionally substituted $R^{21}$;

T is selected from H and —C(O)O$R^3$;
V is —C(O)$R^4$ or —C(O)N$R^{24}R^{25}$,
W is —$(C(R^3)(R^4))_{n2}$—;
X is aryl, wherein said aryl is unsubstituted or optionally independently substituted with one to four selected $R^{20}$ moieties which can be the same or different, each $R^{20}$ moiety being independently selected from the group of $R^{20}$ moieties below,
U is —Y—$(C(R^3)(R^4))_q$—;
Y is —O—;
n is 0 to 2;
n2 is 1 to 2;
q is 1 to 4;
x is 0 to 2;
$R^1$ is heteroaryl, wherein said heteroaryl group of $R^1$ is unsubstituted or optionally independently substituted with one to six $R^{20}$ moieties which can be the same or different, each $R^{20}$ moiety being independently selected from the group of $R^{20}$ moieties below,
each $R^2$, $R^4$ and $R^5$ is the same or different and each is independently selected from the group consisting of H, halo, alkyl, $R^{22}$-substituted alkyl, cycloalkyl, heterocyclyl, arylalkyl, heteroarylalkyl, aryl, heteroaryl, —O$R^6$, —C(O)$R^7$, —C(O)O$R^6$, —N$R^{24}R^{25}$, —N$R^{24}$C(O)$R^{25}$, —N(=C—O—N$R^{24}R^{25}$), —N$R^{24}$S(O)$_2R^{25}$, wherein each of the cycloalkyl, heterocyclyl, arylalkyl, heteroarylalkyl, aryl and heteroaryl groups of $R^2$, $R^4$ and $R^5$ is unsubstituted or optionally independently substituted with one to six alkyl, $R^{22}$-substituted alkyl or $R^{22}$ moieties which can be the same or different, each $R^{22}$ moiety being independently selected from the group of $R^{22}$ moieties below;

each $R^3$ is the same or different and is independently selected from the group consisting of H, alkyl, $R^{22}$-substituted alkyl, cycloalkyl, heterocyclyl, arylalkyl, heteroarylalkyl, aryl, heteroaryl, —O$R^6$, —C(O)$R^7$, —C(O)O$R^6$, —N$R^{24}R^{25}$, —N$R^{24}$C(O)$R^{25}$, —N(=C—O—N$R^{24}R^{25}$) and —N$R^{24}$S(O)$_2R^{25}$, each of the cycloalkyl, heterocyclyl, arylalkyl, heteroarylalkyl, aryl and heteroaryl groups of $R^3$ is unsubstituted or optionally independently substituted with one to four alkyl, $R^{22}$-substituted alkyl or $R^{22}$ moieties which can be the same or different, each $R^{22}$ moiety being independently selected from the group of $R^{22}$ moieties below;

each $R^6$ is independently selected from the group consisting of H, alkyl and —OCF$_3$;

each $R^7$ is independently selected from the group consisting of H, alkyl, heteroaryl and —CF$_3$;

each $R^{20}$ is independently selected from the group consisting of: alkyl, $R^{21}$-substituted alkyl, —O$R^3$, halo, —CN, —NO$_2$, —N$R^{24}R^{25}$, —C(O)$R^3$, —C(O)O$R^3$, —C(O)N$R^{24}R^{25}$, —S(O)$_x$N$R^{24}R^{25}$, —S(O)$_xR^5$, —CF$_3$, —OCF$_3$, —CF$_2$CF$_3$, —C(=NOH)$R^3$, aryl, heteroaryl, cycloalkyl, heterocyclyl, —N($R^{25}$)S(O)$_xR^5$, —N($R^{25}$)C(O)$R^5$, and —N($R^{25}$)C(O)N$R^{24}R^{25}$, wherein each of the aryl, heteroaryl, cycloalkyl and heterocyclyl groups of $R^{20}$ is unsubstituted or optionally independently substituted with one to four $R^{22}$ moieties which can be the same or different, each $R^{22}$ moiety being independently selected from the group of $R^{23}$ moieties below, or two $R^{20}$ groups taken together with the carbon to which both $R^{20}$ groups are attached is

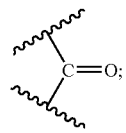

$R^{21}$ is one to three substituents independently selected from the group consisting of: —O$R^3$, halo, —CN, —NO$_2$, —N$R^{24}R^{25}$, —C(O)$R^3$, —C(O)O$R^3$, —C(O)N$R^{24}R^{25}$, —S(O)$_x$N$R^{24}R^{25}$, —SO$_xR^5$, —CF$_3$, —OCF$_3$, —CF$_2$CF$_3$, —C(=NOH)$R^3$, $R^{23}$-substituted alkyl, aryl, heteroaryl, cycloalkyl, heterocyclyl, —N($R^{25}$)S(O)$_xR^5$, —N($R^{25}$)C(O)$R^5$, and —N($R^{25}$)C(O)N$R^{24}R^{25}$;

wherein each of the aryl, heteroaryl, cycloalkyl, and heterocyclyl groups of $R^{21}$ is unsubstituted or optionally independently substituted with one to four $R^{23}$ moieties which can be the same or different, each $R^{23}$ moiety being independently selected from the group of $R^{23}$ moieties below, or two $R^{21}$ groups taken together with the carbon to which both $R^{21}$ groups are attached is

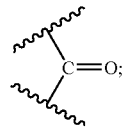

each $R^{22}$ is independently selected from the group consisting of: halo, alkynyl, aryl, heteroaryl, —$OR^{24}$, —($C_1$-$C_6$ alkyl)-$OR^{24}$, —CN, —$NO_2$, —$NR^{24}R^{25}$, —$C(O)R^{23}$, —$C(O)OR^{23}$, —$C(O)NR^{24}R^{25}$, —$S(O)_xNR^{24}R^{25}$, —$S(O)_xR^{23}$, —$CF_3$, —$OCF_3$, —$CF_2CF_3$, —$C(=NOH)R^{23}$, —$N(R^{24})S(O)_xR^{25}$, —$N(R^{24})C(O)R^{25}$, and —$N(R^{24})C(O)NR^{24}R^{25}$, or two $R^{22}$ groups taken together with the carbon to which both $R^{22}$ groups are attached is

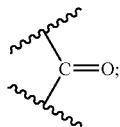

each $R^{23}$ is independently selected from the group consisting of H, hydroxyl, halo and alkyl;

each $R^{24}$ is independently selected from the group consisting of H and alkyl;

each $R^{25}$ is independently selected from the group consisting of H, hydroxyl, alkyl, hydroxyalkyl, aryl, cycloalkyl, heteroaryl, —$NR^{24}R^{24}$, —($C_1$ to $C_6$ alkyl)$NR^{24}N^{24}$, —$CF_3$ and —$S(O)R^{23}$.

In another embodiment, W is —$CH_2$— in formula (I).

In another embodiment, U is —O—$CH_2$— in formula (I).

In another embodiment, U is —$OCH(CO_2CH_3)$— in formula (I).

In another embodiment, T is H in formula (I).

In another embodiment, T is —$C(O)OCH_2CH_3$ in formula (I).

In another embodiment, V is —$C(O)_2H$ in formula (I).

In another embodiment, V is —$C(O)NHOH$ in formula (I).

In another embodiment, in formula (I), M, together with the two carbon atoms to which it is shown attached in formula (I), represents a 5 membered heterocyclyl comprising 1 heteroatom selected from O, N, and S, wherein said 5 membered heterocyclyl is only substituted with the four substituents V, $R^2$, T, and —$(W)_n$—X—U—$R^1$ as set forth in formula (I).

In another embodiment, in formula (I), M, together with the two carbon atoms to which it is shown attached in formula (I), represents a 4 membered heterocyclyl comprising 1 carbonyl group and 1 heteroatom selected from O, N, and S, wherein said 4 membered heterocyclyl is only substituted with the four substituents V, $R^2$, T, and —$(W)_n$—X—U—$R^1$ as set forth in formula (I).

In one embodiment, in formula (II), T is —$C(O)OR^3$, wherein $R^3$ is an alkyl.

In another embodiment, in formula (II), $R^1$ is a heteroaryl with 1 heteroatom selected from S, O and N, wherein said heteroaryl is substituted with a phenyl moiety.

In another embodiment, in formula (II), $R^1$ is a heteroaryl with 1 heteroatom selected from S, O and N, wherein said heteroaryl is substituted with a phenyl moiety, and wherein said heteroaryl is quinolinyl.

In another embodiment, in formula (II), $R^1$ is

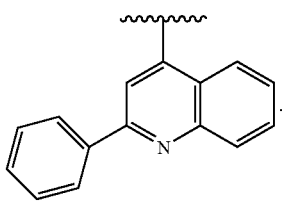

In another embodiment, in formula (II), V is —$(CR^{23}R^{24})_{n1}C(O)NR^{25}OR^3$ wherein n1 is 0, and both $R^3$ and $R^{25}$ are H.

In another embodiment, in formula (II), $R^2=R^4=R^5=H$.

In another embodiment, in formula (II), L is aryl; in another embodiment said aryl is phenyl.

In one embodiment, in formula (III), $G_2$ is H.

In another embodiment, in formula (III), T is H.

In another embodiment, in formula (III), wherein $R^2$ and $R^5$ are both hydrogen.

In another embodiment, in formula (III), one of $R^3$ and $R^4$ is H, and the other is —$C(O)OR^6$.

In another embodiment, in formula (III), both $R^3$ and $R^4$ are H.

In another embodiment, in formula (III), $R^1$ is a heteroaryl with 1 heteroatom selected from S, O and N, wherein said heteroaryl is substituted with a phenyl moiety.

In another embodiment, in formula (III), $R^1$ is a heteroaryl with 1 heteroatom selected from S, O and N, wherein said heteroaryl is substituted with a phenyl moiety, and wherein said heteroaryl is quinolinyl.

In another embodiment, in formula (III), $R^1$ is

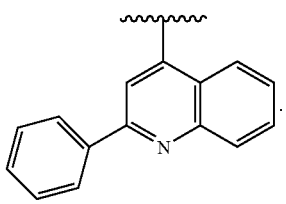

In another embodiment, in formula (III), V is selected from the group consisting of —$(CR^{23}R^{24})_{n1}C(O)OR^3$ and —$(CR^{23}R^{24})_{n1}C(O)NR^{25}OR^3$ wherein n1 is 0 and both $R^3$ and $R^{25}$ are H.

In another embodiment, in formula (III), L is aryl; in another embodiment said aryl is phenyl.

In another embodiment, the compound of formula (I) is selected from the group consisting of:

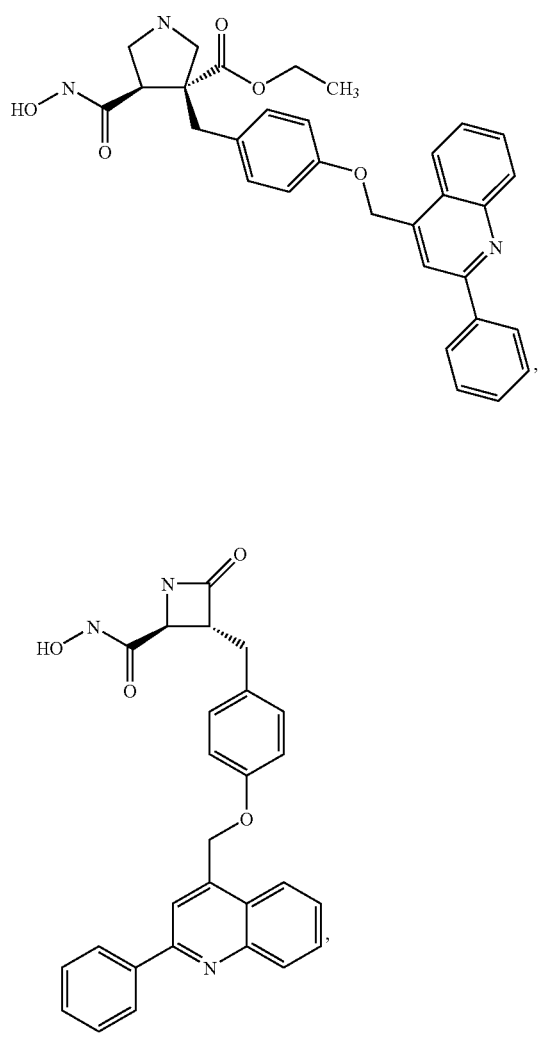
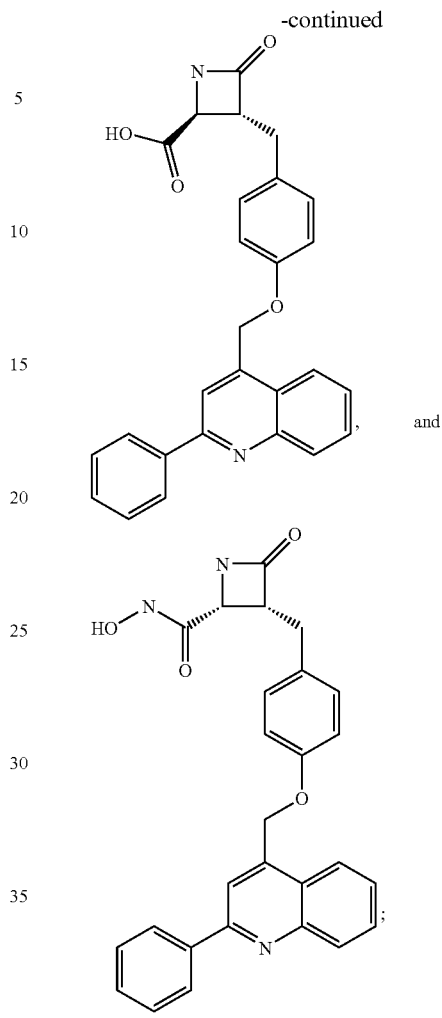
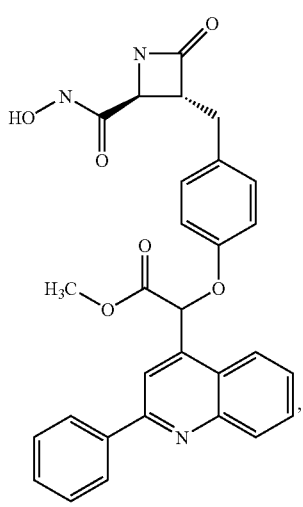

or a pharmaceutically acceptable salt, solvate, or ester thereof.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

The phrase "$R^{21}$-substituted alkyl" means that the alkyl group can be substituted by one or more $R^{21}$ substituents that may be the same or different, each substituent being independently selected from the group consisting of $R^{21}$ substituents listed above. Each of the aryl, halo-substituted aryl, heteroaryl, cycloalkyl and heterocycloalkyl groups of $R^{21}$ can be unsubstituted or independently substituted with one to four independently selected $R^{23}$ moieties which can be the same or different, each $R^{23}$ moiety being independently selected from the group of $R^{23}$ moieties above.

The phrase "$R^{22}$-substituted alkyl" means that the alkyl group can be substituted by one or more $R^{22}$ substituents that may be the same or different, each substituent being independently selected from the group consisting of $R^{22}$ substituents listed above.

The phrase "$R^{52}$-substituted alkyl" means that the alkyl group can be substituted by one or more $R^{52}$ substituents which may be the same or different, each substituent being independently selected from the group consisting of $R^{21}$ substituents listed above.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

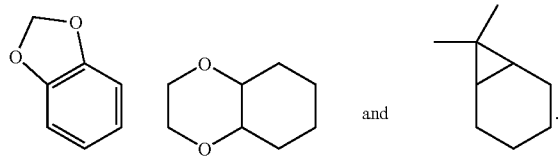

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also include a single moiety (e.g., carbonyl) which simultaneously replaces two available hydrogens on the same carbon atom on a ring system. An example of such a heterocyclyl is pyrrolidone:

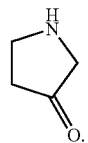

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, dihydroimidazole, dihydrooxazole, dihydrooxadiazole, dihydrothiazole, 3,4-dihydro-2H-pyran, dihydrofuranyl, fluorodihydrofuranyl, 7-oxabicyclo[2.2.1]heptenyl, dihydrothiophenyl, dihydrothiopyranyl, and the like. "Heterocyclenyl" may also include a single moiety (e.g., carbonyl) which simultaneously replaces two available hydrogens on the same carbon atom on a ring system. An example of such a heterocyclenyl is pyrrolidinone:

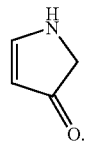

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

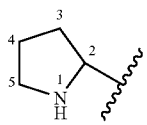

there is no —OH attached directly to carbons marked 2 and 5.

It should also be noted that tautomeric forms such as, for example, the moieties:

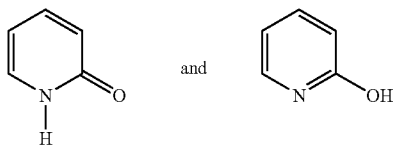

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula (I), (II) or (III), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I), (II), or (III), or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I), (II), or (III) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-(C1-C2)alkyl and piperidino-, pyrrolidino- or morpholino($C_2$-$C_3$) alkyl, and the like.

Similarly, if a compound of Formula (I), (II), or (III) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)$ alkyl$)_2$ or glycosyl (the radical resulting from the removal of a hydroxyl group of the hemiacetal form of a carbohydrate), and the like.

If a compound of Formula (I), (II), or (III) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) alkyl, ($C_3$-$C_7$) cycloalkyl, benzyl, or R-carbonyl is a natural α-aminoacyl or natural α-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$) alkyl and $Y^3$ is ($C_1$-$C_6$)alkyl, carboxy ($C_1$-$C_6$)alkyl, amino($C_1$-$C_4$)alkyl or mono-N— or di-N,N—($C_1$-$C_6$)alkylaminoalkyl, —C($Y^4$)$Y^5$ wherein $Y^4$ is H or methyl and $Y^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula (I), (II), or (III) can form salts which are also within the scope of this invention. Reference to a compound of Formula (I), (II), or (III) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I), (II), or (III) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I), (II), or (III) may be formed, for example, by reacting a compound of Formula (I), (II) or (III) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula (I), (II), and (III) and salts, solvates, esters and prodrugs thereof, may exist in their tautomeric form (for example, as an amide or imino ether). All such tautomeric forms are contemplated herein as part of the present invention.

The compounds of Formula (I), (II), or (III) may contain asymmetric or chiral centers, and, therefore, exist in different stereoisomeric forms. It is intended that all stereoisomeric forms of the compounds of Formula (I), (II), or (III) as well as mixtures thereof, including racemic mixtures, form part of the present invention. In addition, the present invention embraces all geometric and positional isomers. For example, if a compound of Formula (I), (II), or (III) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I), (II), or (III) may be atropisomers (e.g., substituted biaryls) and are considered as part of this invention. Enantiomers can also be separated by use of chiral HPLC column.

It is also possible that the compounds of Formula (I), (II), or (III) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I), (II), or (III) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I), (II), or (III) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I), (II), or (III) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula (I), (II), or (III), and of the salts, solvates, esters and prodrugs of the compounds of Formula (I), (II), or (III), are intended to be included in the present invention.

When a variable appears more than once in the structural formula, for example $R^3$ or $R^5$, the identity of each variable appearing more than once may be independently selected from the definition for that variable.

The compounds of the present invention can have pharmacological properties, for example the compounds of Formula I, II or III can be inhibitors of TACE (TNF-α) and/or MMP activity. The compounds of Formula I, II or III can have anti-inflammatory activity and/or immunomodulatory activity and can be useful in the treatment of diseases including but not limited to septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and/or bronchitis. It is contemplated that a compound of this invention may be useful in treating one or more of the diseases listed.

Additionally, a compound of the present invention may be co-administered or used in combination with disease-modifying antirheumatic drugs (DMARDS) such as methotrexate, azathioprine, leflunomide, pencillinamine, gold salts, mycophenolate mofetil, cyclophosphamide and other similar drugs. They may also be co-administered with or used in combination with NSAIDS such as piroxicam, naproxen, indomethacin, ibuprofen and the like; COX-2 selective inhibitors such as Vioxx® and Celebrex®; immunosuppressives such as steroids, cyclosporin, Tacrolimus, rapamycin and the like; biological response modifiers (BRMs) such as Enbrel®, Remicade®, IL-1 antagonists, anti-CD40, anti-CD28, IL-10, anti-adhesion molecules and the like; and other anti-inflammatory agents such as p38 kinase inhibitors, PDE4 inhibitors, other chemically different TACE inhibitors, chemokine receptor antagonists, Thalidomide and other small molecule inhibitors of pro-inflammatory cytokine production.

Also, a compound of the present invention may be co-administered or used in combination with an H1 antagonist for the treatment of seasonal allergic rhinitis and/or asthma. Suitable H1 antagonists may be, for example, Claritin®, Clarinex®, Allegra®, or Zyrtec®.

In another aspect, the invention provides a method for treating rheumatoid arthritis comprising administering a compound of the formula I, II or III in combination with compound selected from the class consisting of a COX-2 inhibitor e.g. Celebrex® or Vioxx®; a COX-1 inhibitor e.g. Feldene®; an immunosuppressive e.g. methotrexate or cyclosporin; a steroid e.g. β-methasone; and anti-TNF-α compound, e.g. Enbrel® or Remicade®; a PDE IV inhibitor, or other classes of compounds indicated for the treatment of rheumatoid arthritis.

In another aspect, the invention provides a method for treating multiple sclerosis comprising administering a compound of the formula I, II or III in combination with a compound selected from the group consisting of Avonex®, Betaseron, Copaxone or other compounds indicated for the treatment of multiple sclerosis.

TACE activity is determined by a kinetic assay measuring the rate of increase in fluorescent intensity generated by TACE catalyzed cleavage of an internally quenched peptide substrate (SPDL-3). The purified catalytic domain of recombinant human TACE (rhTACEc, Residue 215 to 477 with two mutation (S266A and N452Q) and a 6× His tail) is used in the assay. It is purified from the baculovirus/Hi5 cells expression system using affinity chromatography. The substrate SPDL-3 is an internally quenched peptide (MCA-Pro-Leu-Ala-Gln-Ala-Val-Arg-Ser-Ser-Ser-Dpa-Arg-NH2), with its sequence derived from the pro-TNFα cleavage site. MCA is (7-Methoxycoumarin-4-yl)acetyl. Dpa is N-3-(2,4-Dinitrophenyl)-L-2,3-diaminopropionyl.

A 50 µl assay mixture contains 20 mM HEPES, pH 7.3, 5 mM $CaCl_2$, 100 µM $ZnCl_2$, 2% DMSO, 0.04% Methylcellulose, 30 µM SPDL-3, 70 pM rhTACEc and a test compound. RhTACEc is pre-incubated with the testing compound for 90 min. at 25° C. Reaction is started by addition of the substrate. The fluorescent intensity (excitation at 320 nm, emission at 405 nm) was measured every 45 seconds for 30 min. using a fluorospectrometer (GEMINI XS, Molecular Devices). Rate of enzymatic reaction is shown as Units per second. Effect of a test compound is shown as % of TACE activity in the absence of the compound.

Useful compounds for TACE inhibitory activity can exhibit $K_i$ values of less than about 1000 nm, preferably about 0.01 nm to about 1000 nm, more preferably about 0.1 nm to about 100 nm, more preferably about 0.1 to about 15 nm, and most preferably less that about 15 nm. The TACE inhibitory activity (Ki values) of some representative compounds of the present invention are listed in the "EXAMPLES" section hereinbelow.

The pharmaceutical compositions containing the active ingredient may be in a form suitable for oral use, for example, as tablets, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256, 108; 4,166,452; and 4,265,874 to form osmotic therapeutic tablets for controlled release.

Formulations for oral use may also be presented as hard gelatin capsules wherein the active ingredients is mixed with an inert solid diluent, for example, calcium carbonate, calcium phosphate or kaolin, or a soft gelatin capsules where in the active ingredient is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, e.g., sweetening, flavoring and coloring agents, may also be present.

The pharmaceutical compositions of the invention may also be in the form of an oil-in-water emulsions. The oily phase may be a vegetable oil, e.g., olive oil or arachis oil, or a mineral oil, e.g., liquid paraffin or mixtures of these. Suitable emulsifying agents may be naturally-occurring phosphatides, e.g., soy beans, lecithin, and esters or partial esters derived from fatty acids and hexitol anhydrides, for example, sorbitan monooleate, and condensation products of the said partial esters with ethylene oxide, e.g., polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, e.g., as a solution in 1,3-butane diol. Among the acceptable vehicles and solvents that may be employed are water, Ringer's solution and isotonic sodium chloride solution. In addition, sterile fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of suppositories for rectal administration of the drug. The compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of the invention are employed. (For purposes of this application, topical application shall include mouthwashes and gargles.)

The compounds for the present invention can be administered in the intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of Formula I, II or III useful in the method of the present invention range from 0.01 to 1000 mg per day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four time daily.

The amount of active ingredient that may be combined with the carrier materials to produce single dosage form will vary depending upon the host treated and the particular mode of administration.

It will be understood, however, that the specific dose level for any particular patient will depend upon a variety of factors including the age, body weight, general health, sex, diet, time of administration, route or administration, rate of excretion, drug combination and the severity of the particular disease undergoing therapy.

The compounds of the invention may be produced by processes known to those skilled in the art and as shown in the following reaction schemes and in the preparations and examples described below.

EXAMPLES

The following abbreviations are used in the procedures and schemes: dichloromethane (DCM); tetrabutylammonium bromide (TBAB); Benzyl (Bn); acetonitrile (MeCN); ethyl acetate (EtOAc); Tetrahydrofuran (THF); Trifluoroacetic acid (TFA); 1-hydroxy-7-aza-benzotriazole (HOAt); 1-hydroxylbenzotriazole (HOAt); N-methylmorpholine (NMM); 1-(3-dimethylaminopropyl)-3-ethylcarbodiimide hydrochloride (EDCl); diisopropylethyl amine (DIEA); 1-hydroxybenzotriazole (HOBt); Dimethoxyethane (DME). [1-(chloromethyl)-4-fluoro-1,4-diazoniabicyclo[2.2.2]octane bis (tetrafluoroborate)] (Selectfluor); 4-N,N-dimethylaminopyridine (DMAP); 1,8-diazabicyclo[5,4,0] undec-7-ene (DBU); Saturated (sat.); anhydrous. (anhyd); room temperature (rt); hour (h); Minutes (Min), Retention Time ($R_t$); molecular weight (MW); milliliter (mL); gram (g). milligram (mg); equivalent (eq).

All NMR data were collected on 400 MHz NMR spectrometers unless otherwise indicated. LC-Electrospray-Mass spectroscopy with a C-18 column and 5% to 95% MeCN in water as the mobile phase was used to determine the molecular mass and retention time.

The compounds in the invention may be produced by processes known to those skilled in the art and as shown in the following reaction schemes and in the preparations and examples described below. Table 1 contains the compounds with retention time/observed MW and/or NMR data. The compounds of Table 1 can be obtained using synthetic methods similar to those below as listed in the last column of Table 1 using appropriate reagents known to those skilled in the art.

Method A

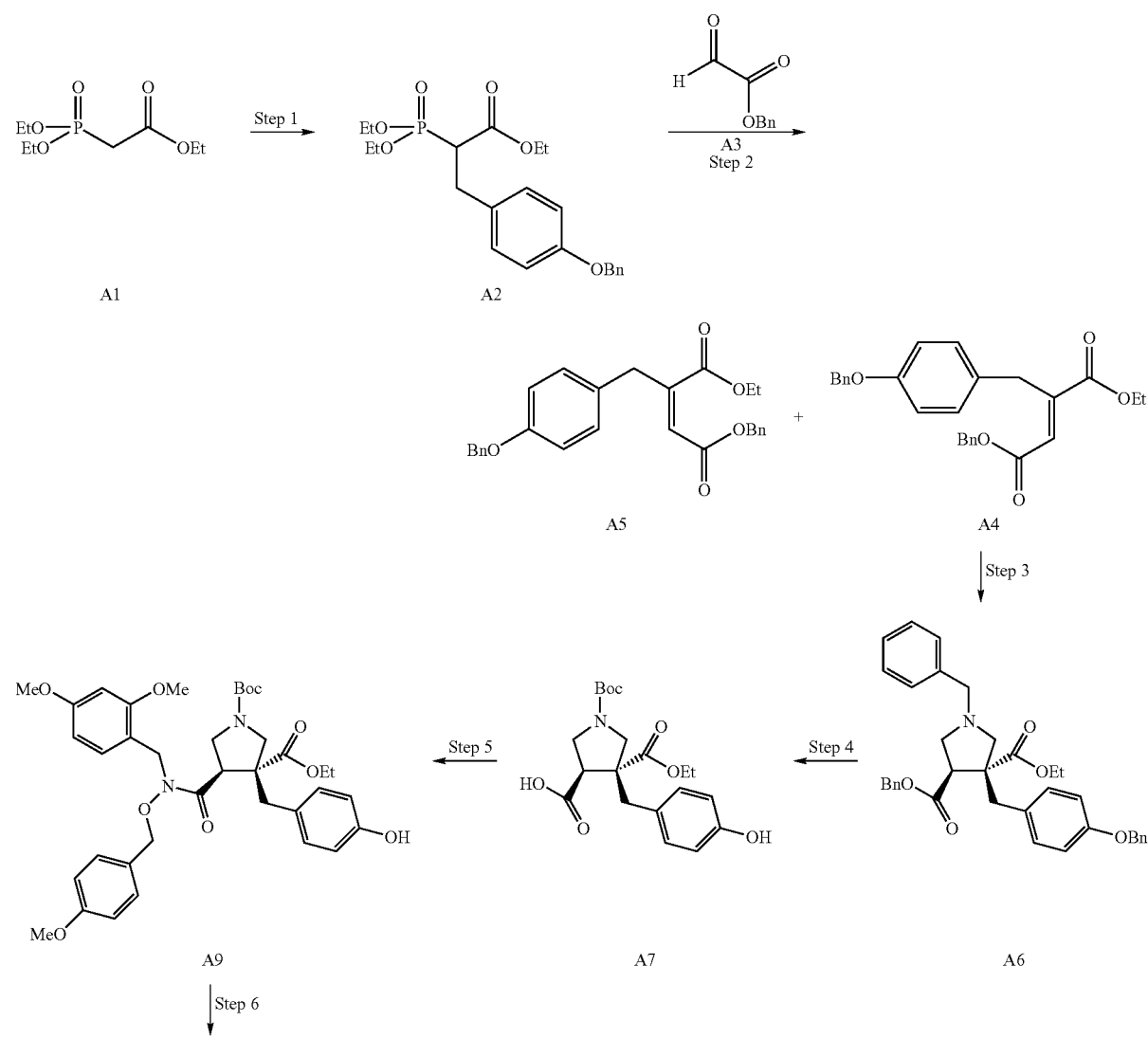

-continued

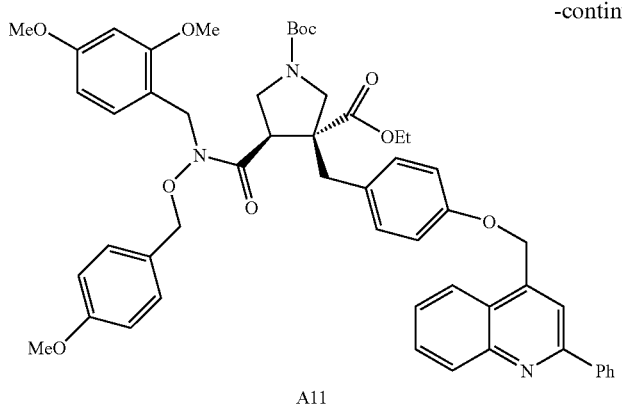

A11

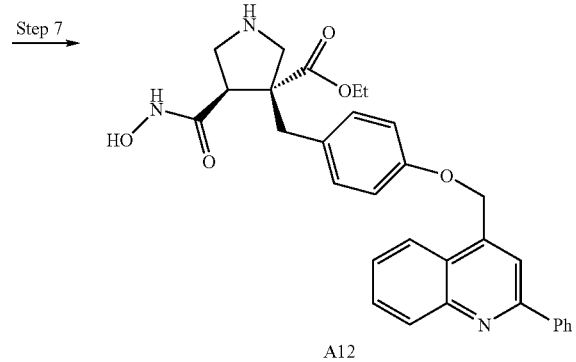

A12

Method A; Step 1

To a suspension of NaH (0.76 g, 31.70 mmol) (washed with pentane 3× and dried under vacuum) in THF (50 mL) was added A1 (5.0 mL, 25 mmol) followed by 4-benzyloxy benzyl chloride (5.75 g, 25 mmol) and tetrabutylammonium iodide (0.500 g). The reaction was stirred at room temperature for 72 hours. The reaction was quenched with $H_2O$ and diluted with EtOAc. The organic phase was removed and the aqueous layer was extracted with EtOAc (2×). The combined organics were washed with brine (1×), dried ($Na_2SO_4$), filtered, and concentrated. The residue was purified by silica gel chromatography (eluting 0% to 100% EtOAc/hexanes) to furnish A2 (1.0 g, 2.4 mmol, 10% yield). MS m/e: 421.1 (M+H).

Method A, Step 2.

To a suspension of NaH (0.009 g, 0.38 mmol) in THF (0.5 mL) at room temperature was added A2 (0.12 g, 0.28 mmol) dropwise as a solution in THF (0.5 mL). The reaction was stirred at room temperature for 15 minutes and A3[1] (0.054 g, 0.33 mmol) was added as a solution in THF (0.5 mL). The resulting mixture was stirred 18 hours. The reaction was quenched with $H_2O$ and diluted with EtOAc. The organic phase was separated, and the aqueous phase was extracted with EtOAc (2×). The combined organics were washed with brine (1×), dried ($Na_2SO_4$), filtered, and concentrated. The residue was purified by silica gel chromatography (eluting 0% to 50% EtOAc/hexanes) to furnish A4 (0.039 g, 0.091 mmol, 32% yield) and A5 (0.042 g, 0.98 mmol, 34% yield). For A4: MS m/e: 431.1 (M+H). For 5: MS m/e: 431.1 (M+H).

[1]Bishop, J. E.; O'Connell, J. F.; Rapoport, H. *J. Org. Chem.* 1991, 56, 5079

Method A Step 3,

To a solution of A4 (0.245 g, 0.57 mmol) and N-(methoxymethyl)-N-(trimethyl-silylmethyl)benzylamine (0.437 mL, 1.71 mmol) in toluene (5 mL) cooled to 0° C. was added TFA (3 drops). The reaction was stirred for 15 minutes at 0° C., and then quenched with 7 N $NH_3$/MeOH (1 mL). The reaction was concentrated, and the residue was purified by reverse phase HPLC (eluting 10:90 to 95:5 $CH_3CN/H_2O$ (0.1% $HCO_2H$)) to furnish A6 (0.29 g, 0.51 mmol, 90% yield) as a white solid. MS m/e: 564.1 (M+H).

Method A Step 4.

A solution of A6 (0.069 g, 0.12 mmol) and 10% Pd/C (25 mg) in MeOH (2 mL)/$CH_2Cl_2$ (1 mL) was stirred at room temperature under an atmosphere of hydrogen for 5 hours. The reaction was filtered through a pad of celite, and the liquid was concentrated. To a solution of the crude mixture in THF (1.5 mL)/$H_2O$ (0.7 mL) was added $NaHCO_3$ (0.036 g, 0.43 mmol) and $(BOC)_2O$ (0.036 g, 0.16 mmol). The reaction was stirred for 18 hours at room temperature. The reaction was diluted with $Et_2O$, and the organic layer was removed. The aqueous phase was acidified with sat. $NH_4Cl$ to about neutral pH and was extracted with EtOAc (3×). The combined organics were dried ($Na_2SO_4$), filtered, and concentrated to provide A7 (0.027 g, 0.69 mmol, 57% yield over 2 steps). MS m/e: 394.1 (M+H).

Method A Step 5.

To a solution of A7 (0.027 g, 0.069 mmol) in $CH_2Cl_2$ (1 mL) cooled to 0° C. was added NMM (0.023 mL, 0.21 mmol), EDCl (0.028 g, 0.15 mmol), and HOAt (0.018 g, 0.13 mmol). This mixture was stirred for 20 minutes and then O-p-Methoxybenzyl-N-2,4-dimethoxybenzylhydroxylamine (0.043 g, 0.14 mmol) was added. The resulting mixture was stirred for 16 hours gradually warming to room temperature. The reaction was quenched with $H_2O$ and diluted with EtOAc. The organic layer was separated, and the aqueous layer extracted with EtOAc (3×). The combined organics were washed with brine (2×), dried ($Na_2SO_4$), filtered, and concentrated. The residue was purified by silica gel chromatography (eluting 0% to 100% EtOAc/hexanes) to furnish A9 (0.032 g, 0.047 mmol, 68% yield). MS m/e: 679.2 (M+H).

Method A Step 6.

To a solution of A9 (0.032 g, 0.047 mmol) in $CH_2Cl_2$ (1 mL) was added $K_2CO_3$ (0.093 g, 0.67 mmol), 2-phenylquinolin-4-yl-methylchloride HCl salt (0.021 g, 0.073 mmol), and tetrabutylammonium iodide (0.005 g, 0.013 mmol). The resulting mixture was stirred for 72 hours at room temperature. At this time, the reaction was quenched with $H_2O$ and diluted with EtOAc. The organic phase was removed, and the aqueous layer was extracted with EtOAc (2×). The combined organics were washed with brine (1×), dried ($Na_2SO_4$), filtered, and concentrated. The residue was purified by silica gel chromatography (eluting 0% to 80% EtOAc/hexanes) to furnish A11 (0.020 g, 0.022 mmol, 48% yield). MS m/e: 896.2 (M+H).

Method A Step 7.

To a solution of A11 (0.016 g, 0.018 mmol) in $CH_2Cl_2$ (0.7 mL) at room temperature was added $Et_3SiH$ (0.012 mL, 0.54 mmol) followed by TFA (0.3 mL). The reaction was stirred for 168 hours, and the reaction was concentrated. The residue was purified by reverse phase HPLC (eluting 5:95 to 95:5 $CH_3CN/H_2O$ (0.1% $HCO_2H$)) to provide A12 (0.006 g, 0.011 mmol, 67% yield) as a white solid. MS m/e: 526.1 (M+H).

Method B
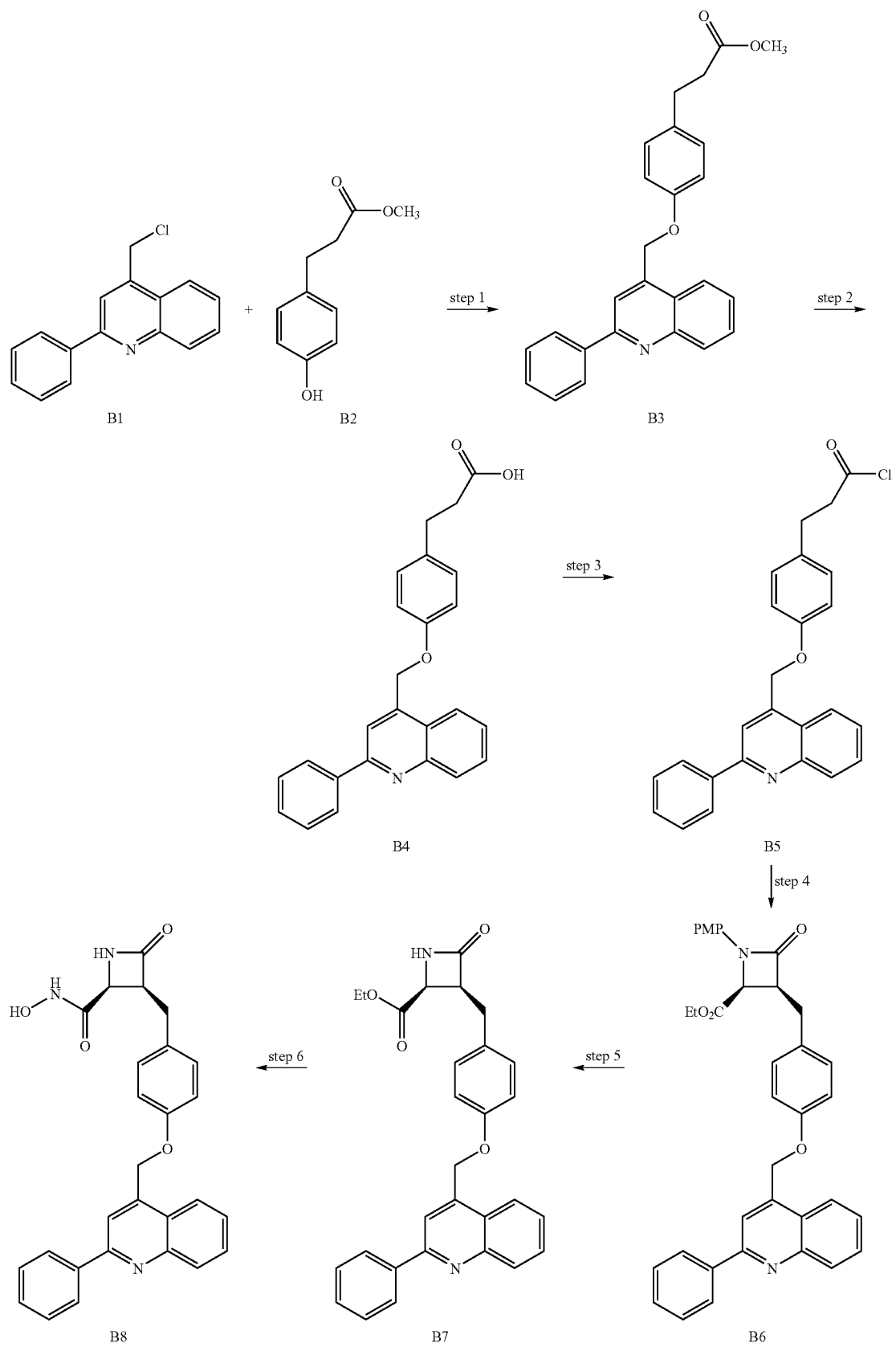

Method B, Step 1.

A mixture of B1 (1.28 g, 6.89 mmol), compound B2 (2.0 g, 6.89 mmol), $Cs_2CO_3$ (4.50 g, 13.8 mmol), and DMF (30 mL) was stirred at room temperature for 16 hours. Saturated aqueous $NaHCO_3$ (100 mL) was added and the aqueous phase was extracted with EtOAc (150 mL). The organic phase was washed with brine (50 mL), dried over $Na_2SO_4$, filtered, and concentrated to give compound B3 (3.1 g).

Method B, Step 2

To a solution of compound B3 (2.5 g, 85%, 6.29 mmol) in THF/water (4:1, 20 mL) was added LiOH (300 mg, 12.5 mmol). The solution was stirred at 35° C. for 2 hours. After cooled to room temperature, it was poured into 1N HCl solution with stirring. A white solid was filtered, washed with water and EtOAc, dried at 45° C. for 8 hours to give compound B4 (2.0 g, 83%).

Method B, Step 3

The solution of compound B4 (1.2 g, 3.1 mmol) and thionyl chloride (6 mL) was heated to 80° C. for three hours. After cooling to room temperature, thionyl chloride was removed with a cold NaOH solution in the solvent receiver. The residue was dried under vacuum for three days to give compound B5 which was used without further purification.

Method B, Step 4

To a solution of (4-methoxy-phenylimino)-acetic acid ethyl ester (Niwa, Y.; Shimizu, M. Journal of the American Chemical Society 2003, 125(13), 3720-3721. 78 mg, 0.40 mmol) and TEA (0.167 mL, 1.20 mmol) in dry $CH_2Cl_2$ (0.5 mL) was added compound B5 (176 mg, 0.40 mmol, in 1 mL $CH_2Cl_2$). The solution was heated to 37° C. to 40° C. for 16 hours. After cooled to room temperature, the solution was subjected to silica gel chromatography (Hexane/EtOAc 3:1) to give compound B6 (7.2 mg, 3.1%).

Method B, Step 5

To a cold solution of compound B6 (27 mg, 0.047 mmol) in $CH_3CN$ (1 mL) was added CAN (77 mg, 0.14 mmol, in 0.5 mL water) at 0° C. followed by another addition of CAN (77 mg, 0.14 mmol, in 0.5 mL water in 15 minutes, more CAN) The solution was stirred at 0° C. for an additional 15 minutes before a saturated aqueous $Na_2SO_3$ solution was added and the aqueous phase was extracted with EtOAc (10 mL) three times. The organic phases were washed with brine (10 mL), dried over $Na_2SO_4$, filtered, and concentrated by rotary evaporator. The product was isolated by prep TLC ($CH_2Cl_2$/MeOH/$NH_3$ 25:1:0.1) to give compound B7 (5.0 mg).

Method B, Step 6

A solution of B7 (5.0 mg), hydroxyamine hydrochloride (15 mg), and DBU (36 mg) in MeOH (0.5 mL) was sonicated for 30 minutes. Solvent was removed by rotary evaporator and the crude product B8 was purified by reverse phase HPLC ($CH_3CN$/water/0.1% $HCO_2H$) to give compound 8 (1.0 mg). MS 454.1 $[M+H]^+$.

Method C

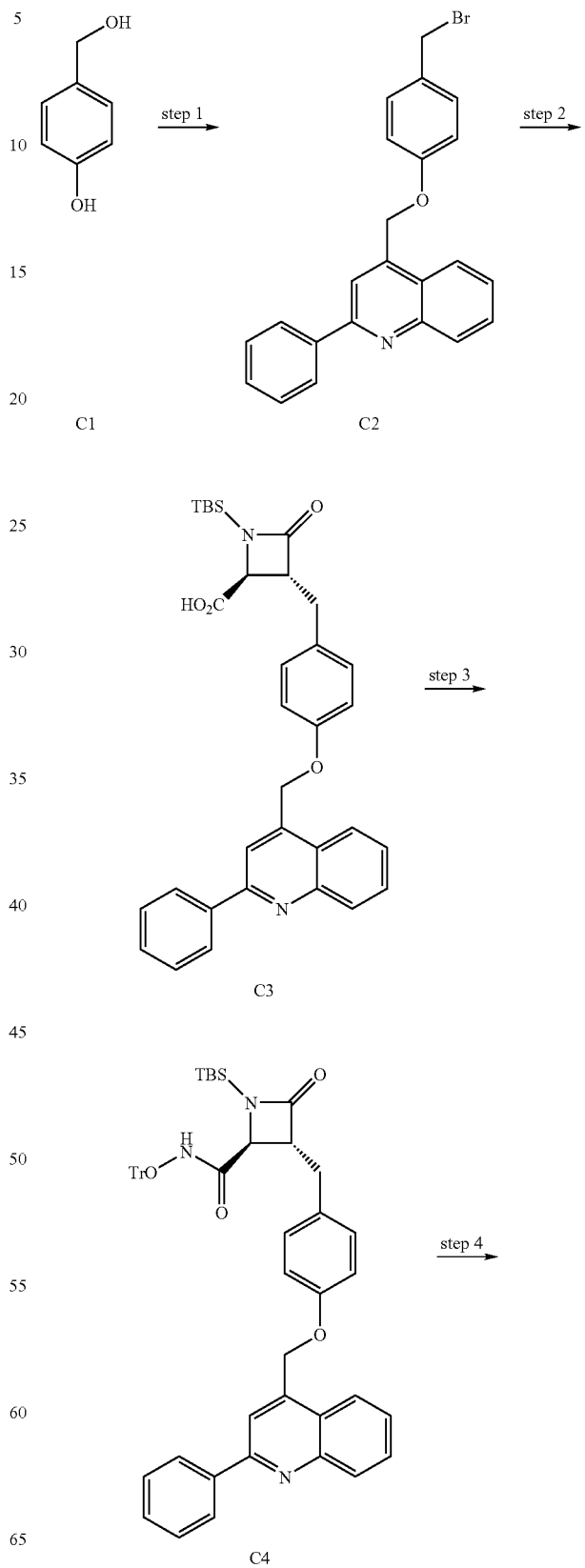

-continued

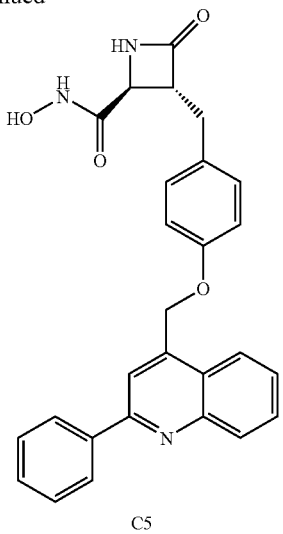

C5

Method C, Step 1.

A solution of Compound C1 (2.14 g, 17.23 mmol), 4-chloromethyl-2-phenyl-quinoline HCl (5.0 g, 17.23 mmol), Cs$_2$CO$_3$ (11.8 g, 36.2 mmol), and dry DMF (60 mL) was stirred at room temperature for 20 hours. A saturated aqueous NaHCO$_3$ solution was added and the aqueous phase was extracted with EtOAc (300 mL). The organic phase was washed with water (100 mL) and brine (100 mL), dried over Na$_2$SO$_4$, filtered, concentrated by rotary evaporator, and dried under vacuum overnight to give [4-(2-phenyl-quinolin-4-ylmethoxy)-phenyl]-methanol (5.81 g, 99%). [4-(2-Phenyl-quinolin-4-ylmethoxy)-phenyl]-methanol (4.0 g, 11.73 mmol) was dissolved in dry CH$_2$Cl$_2$ (60 mL) and was cooled to 0° C. before PBr$_3$ (1.1 mL, 11.73 mmol, in 5 mL CH$_2$Cl$_2$) was added. The solution was stirred overnight at room temperature. The solution was poured into a cold aqueous NaHCO$_3$ solution (250 mL) with stirring. The aqueous phase was extracted with EtOAc (150 mL) four times. The organic phase was washed with brine (50 mL), dried over Na$_2$SO$_4$, filtered, and concentrated by rotary evaporator to give compound C2 (4.3 g, 91%).

Method C, Step 2.

To a solution of 1-(tert-butyl-dimethyl-silanyl)-4-oxo-azetidine-2-carboxylic acid (Baldwin, J. E.; Adlington, R. M.; Gollins, D. W.; Schofield, C. J. Tetrahedron 1990, 46(13-14), 4733-48, 500 mg, 2.18 mmol) in dry THF (10 mL) was added LDA (2M, 2.7 mL, 5.45 mmol) at 0° C. and the reaction was stirred for 15 minutes before the solution was cooled to −20° C. and compound C2 (1.06 gram, 2.62 mmol, in 3 mL THF) was added. The solution was gradually warmed up to 0° C. and stirred at 0° C. for an hour. A cold HCl solution (0.4 M) was added and the aqueous phase was extracted with EtOAc (100 mL) twice. The organic phase was dried over Na$_2$SO$_4$, filtered, and concentrated by rotary evaporator. The product C3 was isolated by silica gel chromatography (CH$_2$Cl$_2$/MeOH/HCO$_2$H: 40:1:0.1 to 20:1:0.1) to give compound 3 (700 mg, 58%).

Method C, Step 3.

A solution of compound C3 (41 mg, 0.074 mmol), TrONH$_2$ (41 mg, 0.15 mmol), EDCl (29 mg, 0.15 mmol), HOBT (20 mg, 0.15 mmol), and NMM (20 mg, 0.2 mmol) in DMF (1 mL) was stirred at room temperature for 16 hours. Water was added and the aqueous phase was extracted with EtOAc. The organic phase was washed with brine, dried over Na$_2$SO$_4$, filtered, and concentrated by rotary evaporator. The product was isolated by prep silica gel TLC (CH$_2$Cl$_2$/MeOH: 40:1) to give compound C4 (17 mg).

Method C, Step 4.

To a solution of compound C4 (17 mg) in CH$_2$Cl$_2$ was added Et$_3$SiH (two drops) and TFA (two drops) at room temperature. Three minutes later, the solvent was removed by rotary evaporator. The product was isolated by prep silica gel TLC (CH$_2$Cl$_2$/MeOH 10:1) twice to give compound C5 (4.2 mg). MS: 454.1 [M+H]$^+$.

Method D

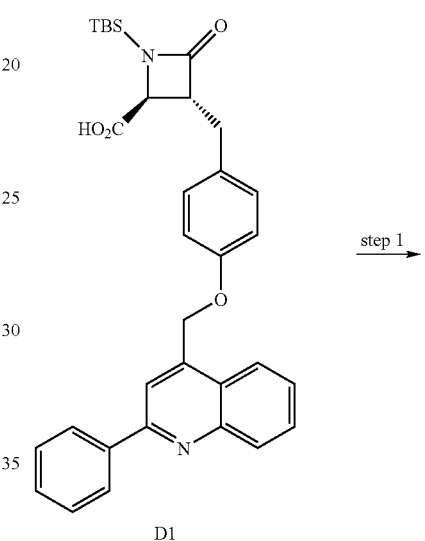

D1

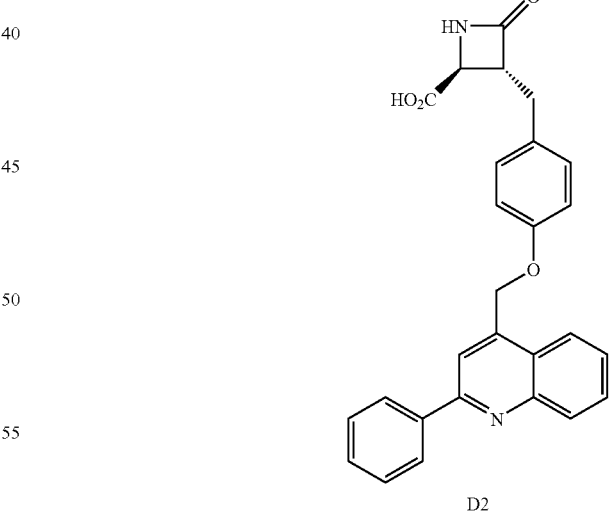

D2

Method D, Step 1

To a solution of compound D1 (34 mg, 0.06 mmol) in THF was added TBAF (1M in THF, 0.07 mL, 0.07 mmol) at 0° C. Five minutes later, the solvent was removed by rotary evaporator and the product was isolated by silica gel chromatography (CH$_2$Cl$_2$/MeOH/HCO$_2$H: 10:1:0.1) to give compound D2 (14.0 mg). MS 439.1 [M+H]$^+$.

Example E

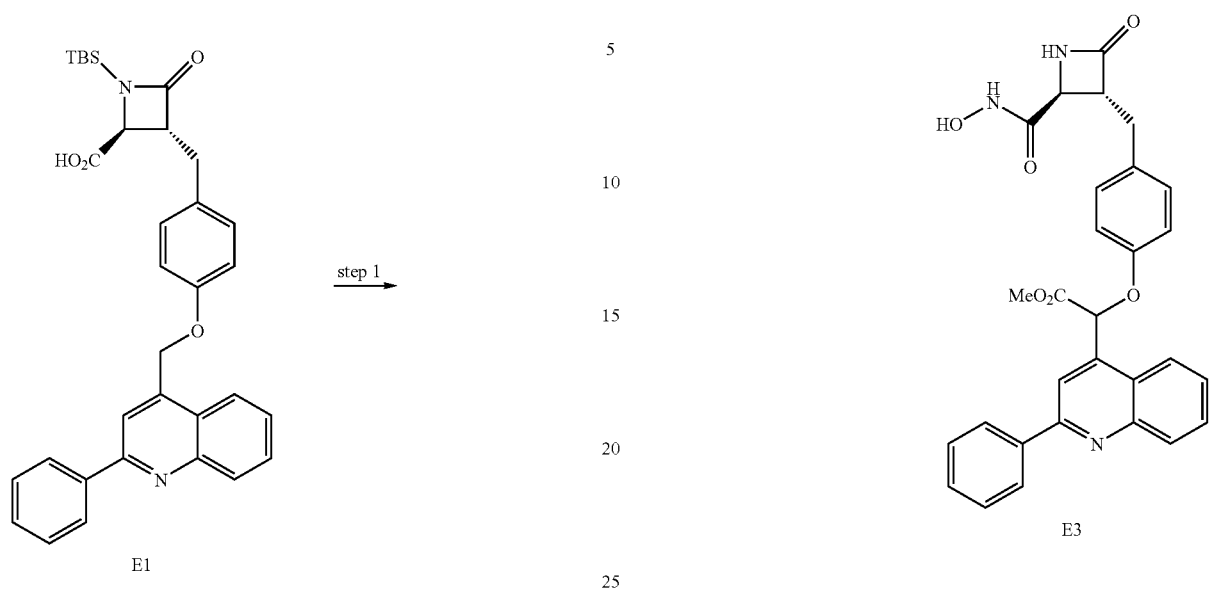

Method E, Step 1

To a solution of compound E1 (60 mg, 0.11 mmol) in dry THF (1 mL) was added LDA (2M, 0.16 mL, 0.33 mmol) at −30° C. The solution was warmed up to 0° C. in 5 minutes and stirred at 0° C. for 10 minutes. It was recooled to −40° C. and methyl cyano formate (0.026 mL, 0.33 mmol) was added. The solution was gradually warmed up to 0° C. in two hours. 0.4N HCl solution was added. The aqueous phase was extracted with EtOAc (10 mL). The organic phase was dried over $Na_2SO_4$, filtered, and concentrated by rotary evaporator. The crude product was purified by silica gel chromatography ($CH_2Cl_2$/MeOH/$HCO_2H$: 40:1:0.1 to 20:1:0.1) to give compound E2 (35 mg).

Compound E3 was prepared in a similar manner as described in Method C. MS: 512.1 $[M+H]^+$.

Method F

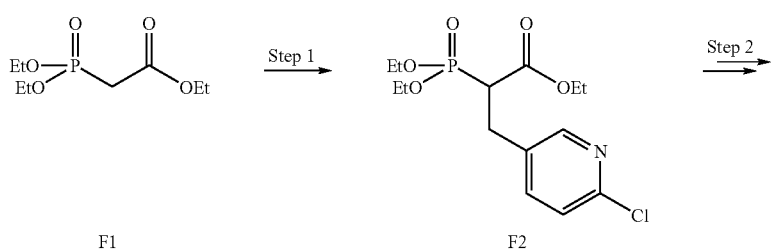

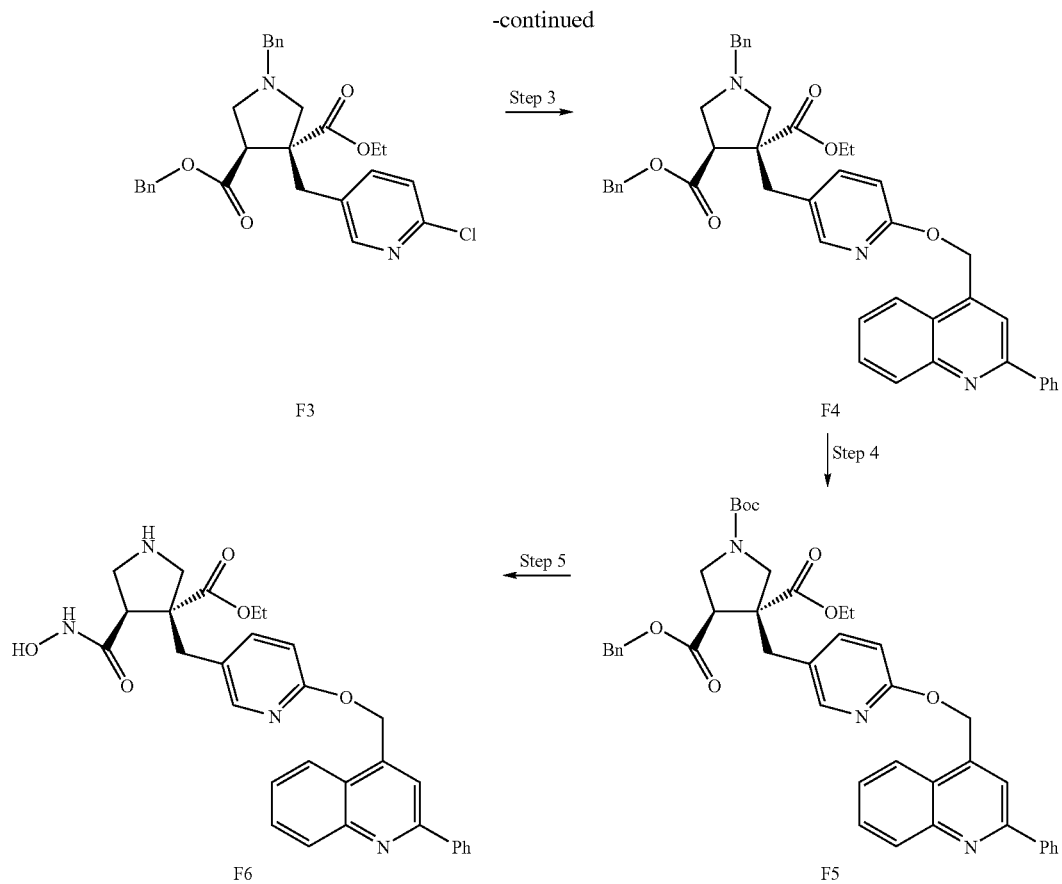

F3  F4  F6  F5

Method F; Step 1

Compound F2 is generated using procedures similar to Method A Step 1.

Method F; Step 2.

Compound F3 is generated using procedures similar to method A step 2 and 3.

Method F; Step 3.

Compound F4 is generated using a literature procedure (JACS, 123, 2001, 10770).

To a toluene solution of 2-phenylquinolin-4-yl-methanol (0.3 mmol) is added F3 (0.150 mmol), Cs$_2$CO$_3$ (0.375 mmol), palladium acetate (12 mg) and 1,1'-binaphthyl-2-yl-di-t-butyl phosphine (30 mg). The reaction mixture is flushed with Nitrogen followed by heating at 110° C. overnight. The reaction mixture is then cooled to r.t. before it is chromatographed via a silica gel column to give F4.

Method F Step 4,

To a DCM solution of F4 is added 1-chloroethyl chloroformate (2 eq) and proton sponge (3 eq). After the reaction was stirred overnight, it is quenched with aq. potassium bicarbonate until the mixture pH reaches 9. To the mixture is added Boc anhydride and the reaction mixture is stirred overnight before it is extracted with DCM. The organic solution is dried and the solvent evaporated. The residue is chromatographed via a silica gel column to give the desired product F5.

Method F Step 5.

Compound F5 is obtained using procedures similar to Method A, Step 4, 5 and 7.

In the table below, those compounds having a Ki value of less than 20 nM (<20 nM) are designated with letter "A"; those with a Ki value of from 20 to less than 100 nM (10-<100 nM) are designated with letter "B"; those with a Ki value of from 100 to 1000 nM are designated with letter "C"; and those with a Ki value of more than 1000 nM (>1000 nM) are designated with letter "D".

| Compound # | Structure | Ki |
|---|---|---|
| A12 | 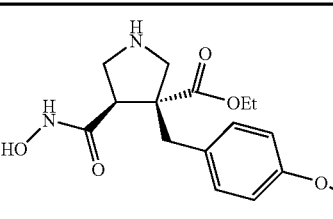 | B |

-continued

| Compound # | Structure | Ki |
|---|---|---|
| C5 | (structure) | B |
| D2 | (structure) | E |
| E3 | (structure) | C |

-continued

| Compound # | Structure | Ki |
|---|---|---|
| B8 | (structure) | A |

Specific TACE inhibitory activity (Ki values) of some representative compounds of the present invention are set forth below.

| Compound # | Structure | Ki |
|---|---|---|
| B8 | (structure) | 11.7 |

-continued

| Compound # | Structure | Ki |
|---|---|---|
| C5 | 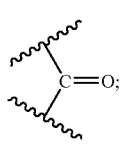 | 55 |
| A12 | 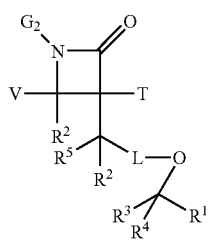 | 59 |

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

We claim:

1. A compound represented by the structural formula (III):

or a pharmaceutically acceptable salt of said compound, wherein:

L is aryl or heteroaryl;

$R^1$ is

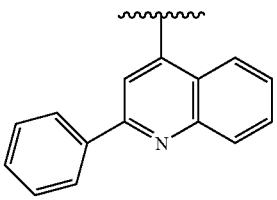

T is H;
$G_2$ is H,
V is selected from the group consisting of —C(O)OH and —C(O)N(H)OH;
x is 0 to 2;
each of $R^2$, $R^4$ and $R^5$ is the same or different and each is independently selected from the group consisting of H, halo, alkyl, $R^{22}$-substituted alkyl, cycloalkyl, heterocyclyl, arylalkyl, heteroarylalkyl, aryl, heteroaryl, —$OR^6$, —$C(O)R^7$, —$C(O)OR^6$, —$NR^{24}R^{25}$, —$NR^{24}C(O)R^{25}$, —N(=C—O—$NR^{24}R^{25}$), —$NR^{24}S(O)_2R^{25}$, wherein each of the cycloalkyl, heterocyclyl, arylalkyl, heteroarylalkyl, aryl and heteroaryl groups of $R^2$, $R^4$ and $R^5$ is unsubstituted or optionally independently substituted with one to six alkyl, $R^{22}$-substituted alkyl or $R^{22}$ moieties which can be the same or different, each $R^{22}$ moiety being independently selected from the group of $R^{22}$ moieties below;

each $R^3$ is the same or different and is independently selected from the group consisting of H, alkyl, $R^{22}$-substituted alkyl, heterocyclyl, arylalkyl, heteroarylalkyl, aryl, heteroaryl, —$OR^6$, —$C(O)R^7$, —$C(O)OR^6$, —$NR^{24}R^{25}$, —$NR^{24}C(O)R^{25}$, —N(=C—O—$NR^{24}R^{25}$) and —$NR^{24}S(O)_2R^{25}$, wherein each of the cycloalkyl, heterocyclyl, arylalkyl, heteroarylalkyl, aryl and heteroaryl groups of $R^3$ is unsubstituted or optionally independently substituted with one to four alkyl, $R^{22}$-substituted alkyl or $R^{22}$ moieties which can be the same or different, each $R^{22}$ moiety being independently selected from the group of $R^{22}$ moieties below;

each $R^6$ is independently selected from the group consisting of H, alkyl and —$OCF_3$;

each $R^7$ is independently selected from the group consisting of H, alkyl, heteroaryl and —$CF_3$;

each $R^{22}$ is independently selected from the group consisting of:
halo, alkynyl, aryl, heteroaryl, —$OR^{24}$, —($C_1$-$C_6$ alkyl)-$OR^{24}$, —CN, —$NO_2$, —$NR^{24}R^{25}$, —$C(O)R^{23}$, —$C(O)OR^{23}$, —$C(O)NR^{24}R^{25}$, —$S(O)_xNR^{24}R^{25}$, —$S(O)_xR^{23}$, —$CF_3$, —$OCF_3$, —$CF_2CF_3$, —C(=NOH)$R^{23}$, —N($R^{24}$)$S(O)_xR^{25}$, —N($R^{24}$)C(O)$R^{25}$, and —N($R^{24}$)C(O)N$R^{24}R^{25}$, or two $R^{22}$ groups taken together with the carbon to which both $R^{22}$ groups are attached is each $R^{23}$ is independently selected from the group consisting of H, hydroxyl, halo and alkyl;
each $R^{24}$ is independently selected from the group consisting of H and alkyl; and each $R^{25}$ is independently selected from the group consisting of H, hydroxyl, alkyl, hydroxyalkyl, aryl, cycloalkyl, heteroaryl, —$NR^{24}R^{24}$, —($C_1$ to $C_6$ alkyl)$NR^{24}N^{24}$, —$CF_3$ and —$S(O)_xR^{23}$.

2. The compound according to claim 1, wherein $R^2$ and $R^5$ are both hydrogen.

3. The compound according to claim 1, wherein one of $R^3$ and $R^4$ is H, and the other is —$C(O)OR^6$.

4. The compound according to claim 1, wherein both $R^3$ and $R^4$ are H.

5. The compound according to claim 1, wherein L is aryl.

6. The compound according to claim 5, wherein said aryl is phenyl.

7. A compound according to claim 1, selected from the group consisting of:

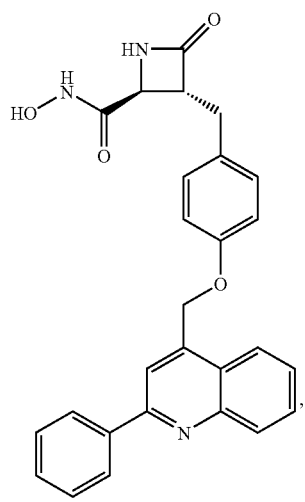

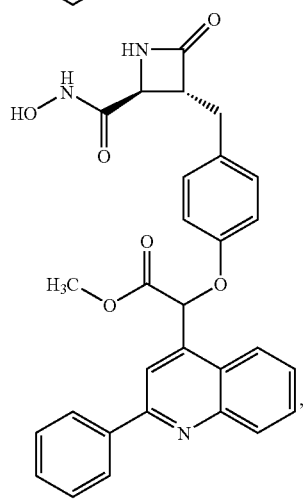

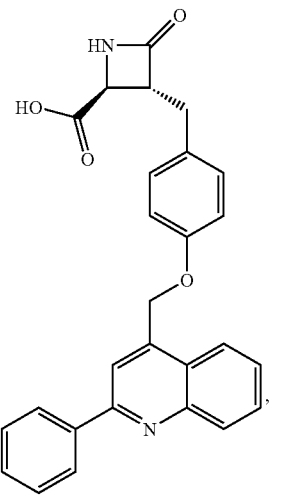

and

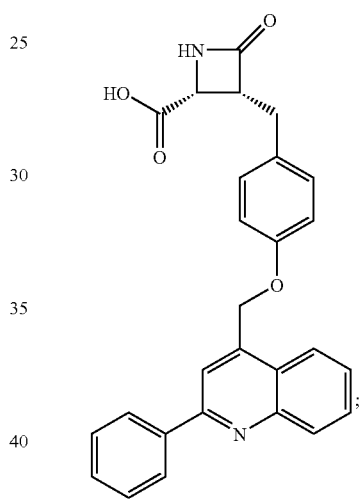

or a pharmaceutically acceptable salt thereof.

8. A pharmaceutical composition comprising a therapeutically effective amount of at least one compound according to claim 1, or a pharmaceutically acceptable salt thereof, in combination with at least one pharmaceutically acceptable carrier.

9. The pharmaceutical composition of claim 8, additionally comprising an anti-inflammatory agent.

* * * * *